(12) United States Patent
Ovzinsky et al.

(10) Patent No.: US 11,395,898 B2
(45) Date of Patent: Jul. 26, 2022

(54) AIR DELIVERY CONDUIT

(71) Applicant: RESMED LIMITED, Bella Vista (AU)

(72) Inventors: Grant Milton Ovzinsky, Sydney (AU); Justin John Formica, Sydney (AU); Jessica Lea Dunn, Sydney (AU); Aaron Samuel Davidson, Sydney (AU); Joseph Samuel Ormrod, Sydney (AU); Jose Ignacia Romagnoli, Sydney (AU); Gerard Michael Rummery, Sydney (AU); Kai Stuebiger, Sydney (AU); Lance Ian Swift, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 803 days.

(21) Appl. No.: 16/355,150

(22) Filed: Mar. 15, 2019

(65) Prior Publication Data

US 2019/0209799 A1     Jul. 11, 2019

Related U.S. Application Data

(63) Continuation of application No. 15/669,173, filed on Aug. 4, 2017, now Pat. No. 10,279,138, which is a
(Continued)

(51) Int. Cl.
     *A61M 16/08*      (2006.01)
     *A61M 16/06*      (2006.01)
     *A61M 16/00*      (2006.01)

(52) U.S. Cl.
     CPC .... *A61M 16/0875* (2013.01); *A61M 16/0066* (2013.01); *A61M 16/06* (2013.01); *A61M 16/0605* (2014.02); *A61M 16/0666* (2013.01); *A61M 16/0672* (2014.02); *A61M 16/0683* (2013.01); *A61M 16/0816* (2013.01); *A61M 2205/02* (2013.01); *A61M 2205/0238* (2013.01);
(Continued)

(58) Field of Classification Search
     CPC ........... A61M 16/06–0694; A61M 2016/0661; A61M 16/08–0891
     See application file for complete search history.

(56) References Cited

U.S. PATENT DOCUMENTS 3,299,908 A     1/1967     Petzetakis
4,478,661 A *     10/1984     Lewis ................. B29C 66/4322
                                                                   138/119
(Continued)

FOREIGN PATENT DOCUMENTS

EP           1731083          12/2006
EP           2 233 816          9/2010
(Continued)

OTHER PUBLICATIONS

International Search Report issued for PCT/AU2012/000667 dated Oct. 4, 2012.
(Continued)

*Primary Examiner* — Valerie L Woodward
(74) *Attorney, Agent, or Firm* — Nixon & Vanderhye P.C.

(57) ABSTRACT

An air delivery conduit includes first and second conduit portions that cooperate to form the conduit, each conduit portion including an inner layer of a film laminate that forms an interior surface of the conduit and an outer layer of a textile that forms an exterior surface of the conduit.

24 Claims, 35 Drawing Sheets

Related U.S. Application Data continuation of application No. 14/124,878, filed as application No. PCT/AU2012/000667 on Jun. 8, 2012, now Pat. No. 9,731,090.

(60) Provisional application No. 61/635,351, filed on Apr. 19, 2012, provisional application No. 61/457,810, filed on Jun. 8, 2011.

(52) U.S. Cl.
CPC . *A61M 2205/0266* (2013.01); *A61M 2205/42* (2013.01); *A61M 2207/00* (2013.01); *A61M 2210/0618* (2013.01); *Y10T 29/49826* (2015.01)

(56) References Cited

U.S. PATENT DOCUMENTS

| | | |
|---|---|---|
| 2002/0002976 A1 | 1/2002 | Smith et al. |
| 2003/0075228 A1 | 4/2003 | Tippett |
| 2003/0154980 A1 | 8/2003 | Berthon-Jones et al. |
| 2004/0226566 A1 | 11/2004 | Gunaratnam |
| 2005/0061326 A1 | 3/2005 | Payne |
| 2005/0069666 A1 * | 3/2005 | Ferrand .......... H02G 3/0481 428/347 |
| 2006/0218702 A1 | 10/2006 | Santos |
| 2007/0246043 A1 | 10/2007 | Kwok |
| 2008/0011305 A1 | 1/2008 | Chandran |
| 2008/0047560 A1 | 2/2008 | Veliss |
| 2008/0060649 A1 | 3/2008 | Veliss et al. |
| 2008/0142003 A1 | 6/2008 | Depel |
| 2008/0173305 A1 | 7/2008 | Frater |
| 2009/0050157 A1 | 2/2009 | Bateman et al. |
| 2010/0018534 A1 | 1/2010 | Veliss et al. |
| 2014/0102456 A1 | 4/2014 | Ovizinsky et al. |
| 2015/0083131 A1 | 3/2015 | Mals |
| 2017/0312465 A1 | 11/2017 | Kwok et al. |
| 2017/0333662 A1 | 11/2017 | Ovzinsky |

FOREIGN PATENT DOCUMENTS

| | | | |
|---|---|---|---|
| JP | 2006-116734 A | 5/2006 | |
| WO | WO 2006/047818 | 5/2006 | |
| WO | WO 2007/009182 | 1/2007 | |
| WO | WO 2007/109837 | 10/2007 | |
| WO | WO 2008/011683 | 1/2008 | |
| WO | WO 2008/070929 | 6/2008 | |
| WO | WO-2011017763 A1 * | 2/2011 | ........ A61M 16/0066 |
| WO | WO 2011/022779 | 3/2011 | |
| WO | WO 2012/122601 | 9/2012 | |
| WO | WO 2012/167327 A1 | 12/2012 | |

OTHER PUBLICATIONS

Hydrospace, NIRI, The Nonwovens Innovation & Research Institute, http://www.nonwovens-innovation.com/hydrospace.html, May 3, 2011, 1 page.
Extended European Search Report dated Feb. 27, 2015 issued in corresponding European Application No. 12796616.6 (10 pages).
A Communication Pursuant to Article 94(3) dated Sep. 8, 2017, in a corresponding European Application No. 12 796 161.6 (5 pages).
EP Search Report dated Apr. 14, 2021 in corresponding EP Application 20198992.8 (7 pages).

* cited by examiner

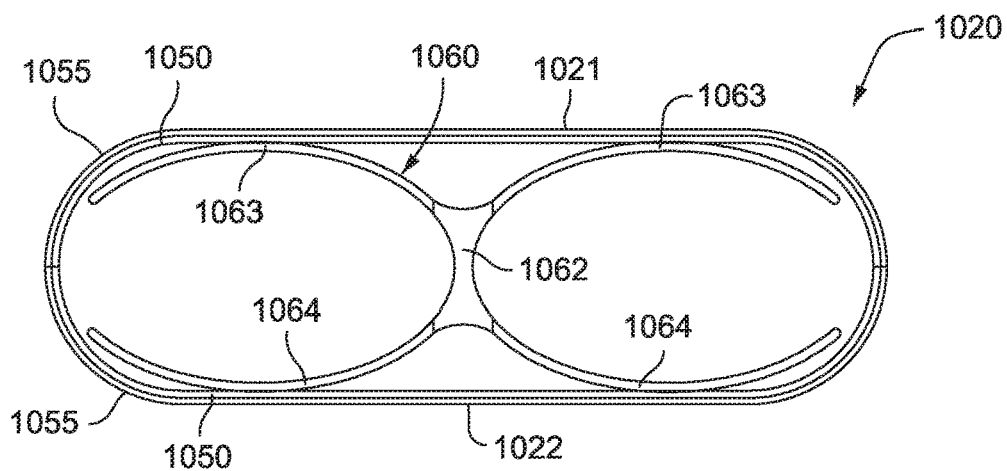
FIG. 38
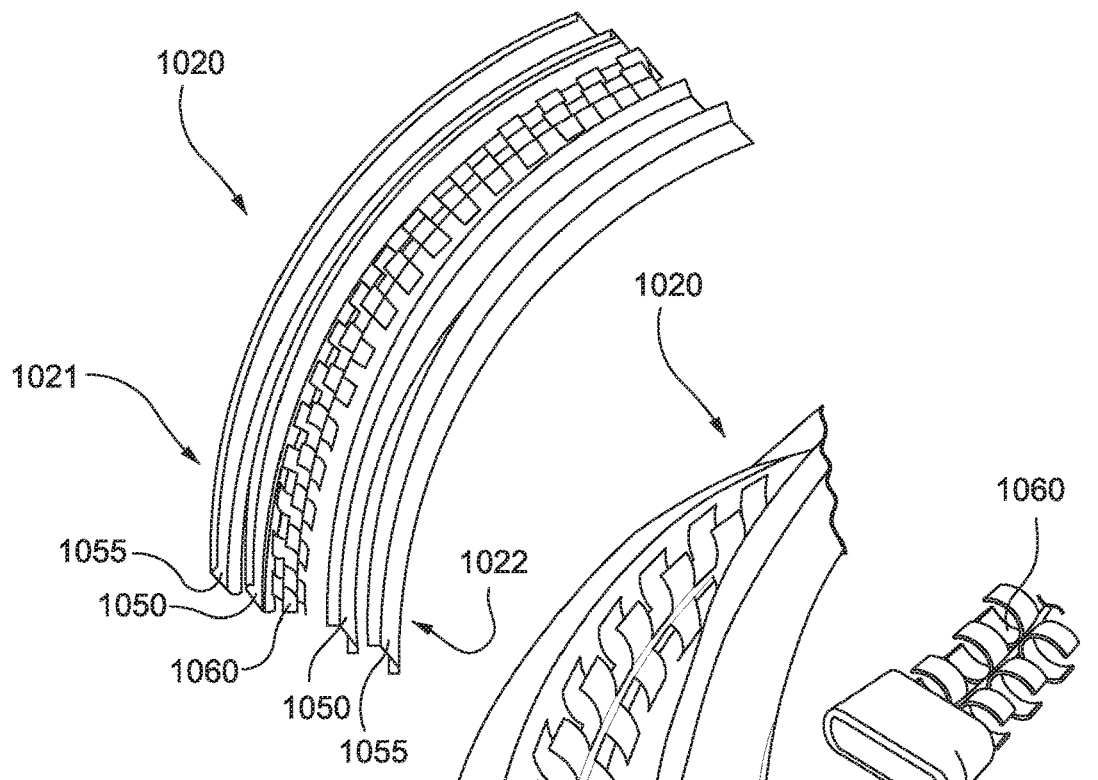
FIG. 39
FIG. 40-1
FIG. 40

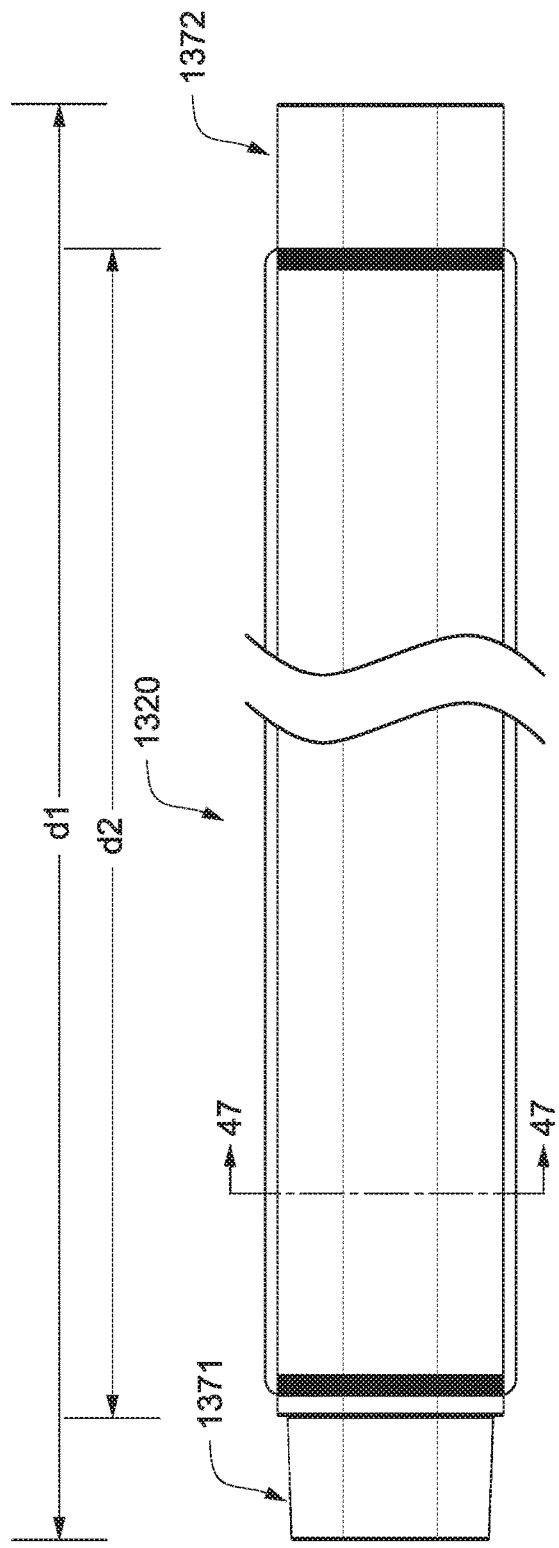
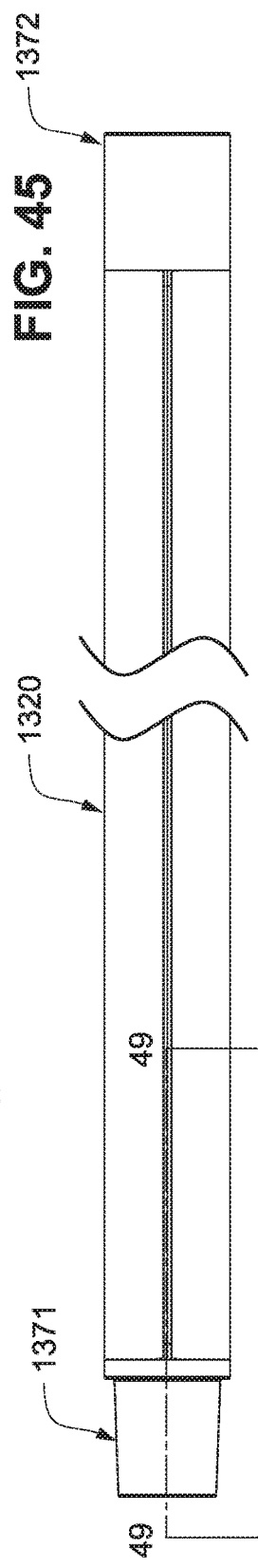
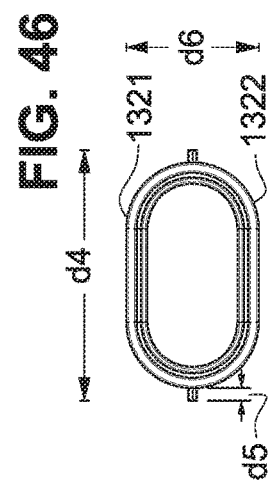
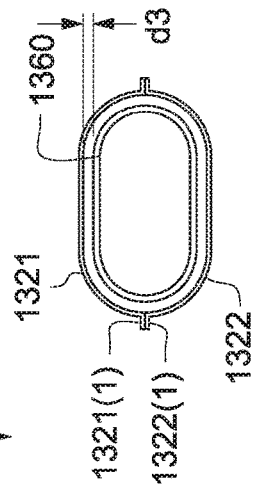

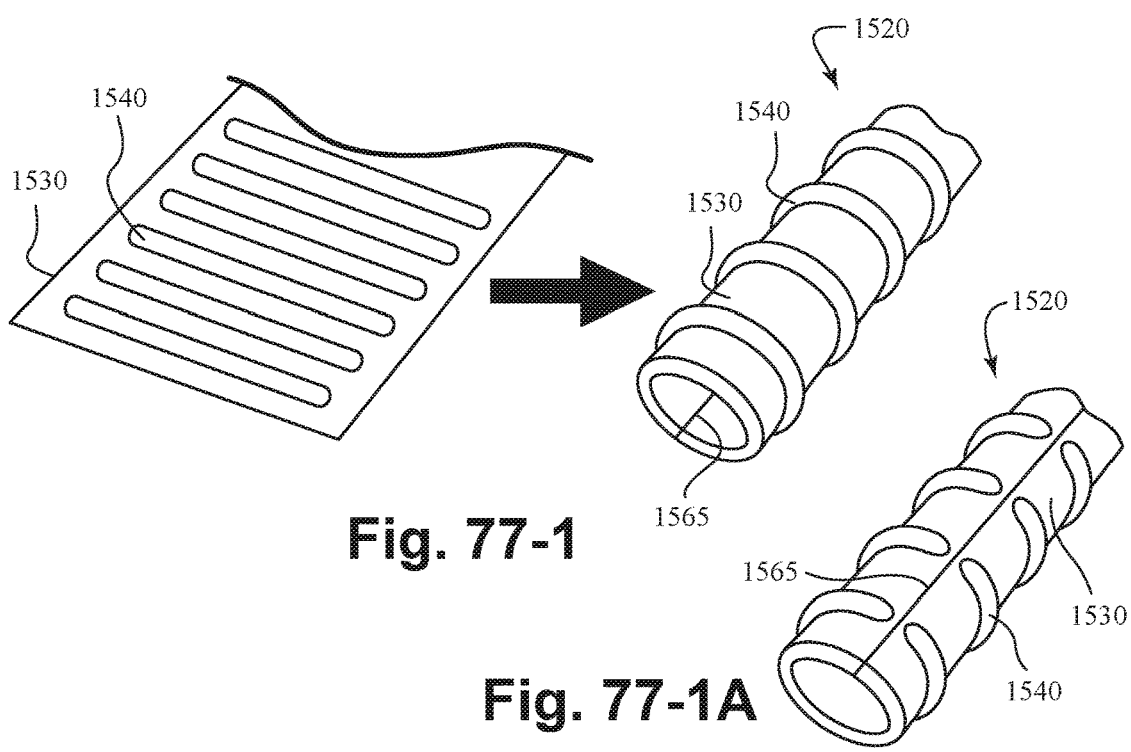
Fig. 77-1
Fig. 77-1A
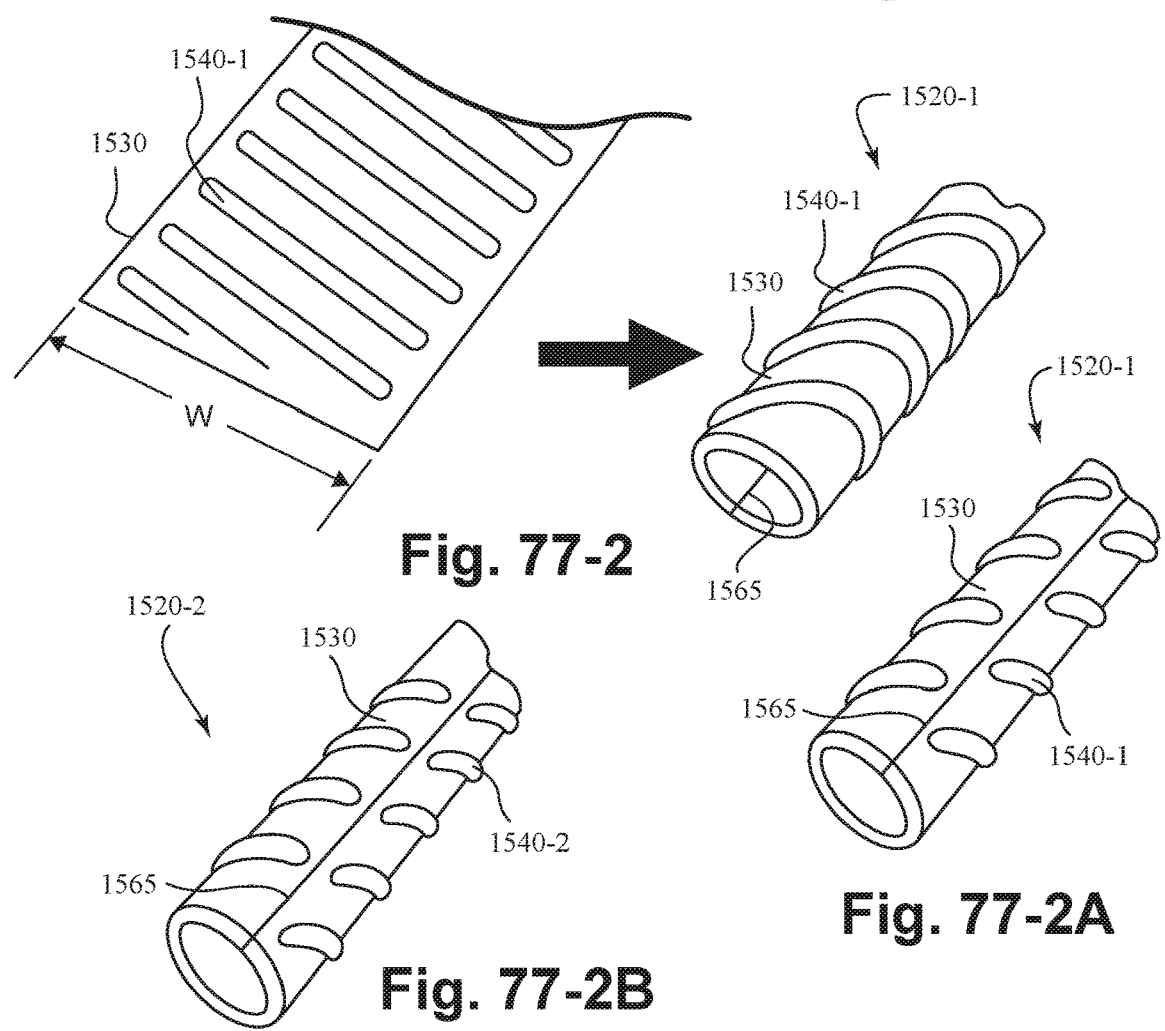
Fig. 77-2
Fig. 77-2A
Fig. 77-2B

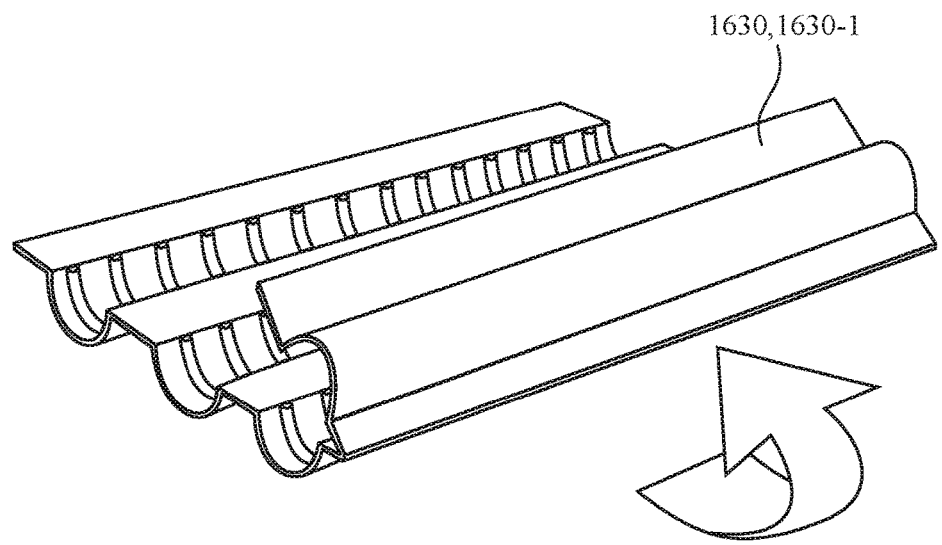
Fig. 78-3
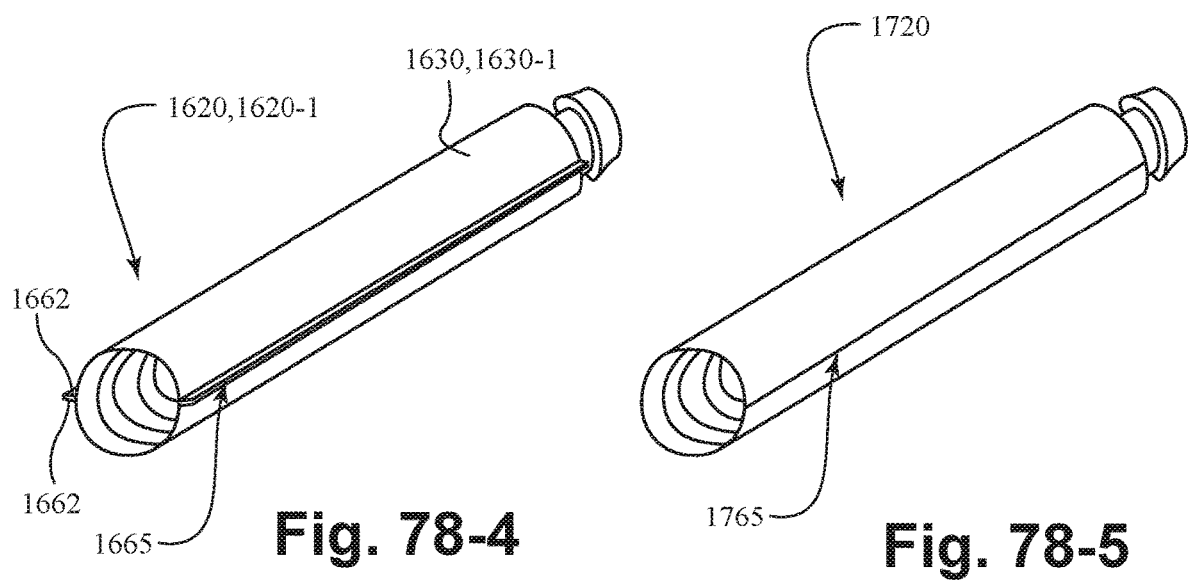
Fig. 78-4  Fig. 78-5

AIR DELIVERY CONDUIT

CROSS-REFERENCE TO APPLICATION

This application is a continuation of U.S. patent application Ser. No. 15/669,173 filed Aug. 4, 2017, now allowed, which is a continuation of U.S. Pat. No. 9,731,090 issued Aug. 15, 2017, which was the U.S. national phase of International Application No. PCT/AU2012/000667, filed Jun. 8, 2012, which designated the U.S. and claimed the benefit of U.S. Provisional Application No. 61/457,810, filed Jun. 8, 2011 and U.S. Provisional Application No. 61/635,351, filed Apr. 19, 2012. Each application mentioned above is hereby incorporated herein by reference in its entirety.

FIELD OF TECHNOLOGY

The present technology relates to air delivery conduits used in Positive Airway Pressure (PAP) systems for treatment, e.g., of Sleep Disordered Breathing (SDB) with Continuous Positive Airway Pressure (CPAP) or Non-Invasive Positive Pressure Ventilation (NIPPV).

BACKGROUND OF TECHNOLOGY

PAP systems to deliver breathable gas to a patient typically include a positive airway pressure (PAP) device, an air or gas delivery conduit, and a patient interface. In use, the air delivery conduit delivers pressurized air or gas from the PAP device to the patient interface in contact with the patient's face.

The present technology provides improvements to known air delivery conduits.

SUMMARY OF TECHNOLOGY

One aspect of the disclosed technology relates to an air delivery conduit for use in the delivery of a supply of air or breathable gas to a patient, e.g., for treatment of respiratory disorders.

Another aspect of the disclosed technology relates to an air delivery conduit in the form of conduit headgear structured to be worn on the patient's head in use and at least partially support a patient interface in a desired position on the patient's face in use.

Another aspect of the disclosed technology relates to an air delivery conduit that is comfortable, occlusion resistant, kink resistant, and/or low cost. For example, the air delivery conduit may be sufficiently comfortable to lie on and adapted to provide a supply of air at pressure when a portion is being lain on by the patient.

Another aspect of the disclosed technology relates to an air delivery conduit that includes three-dimensional shaping to provide minimal assembly complexity, minimal possibility of occlusion by kink and/or compression force, and/or out-of-box intuitiveness (e.g., shape holding, easy to fit and adjust with little or no adjustment). For example, the air delivery conduit may include structural integrity or a self-holding form so it holds the conduit's shape, e.g., shape memory, whether the conduit is on or off the patient's head.

Another aspect of the disclosed technology relates to an air delivery conduit that is formed of one or more materials that provide intimate and comfortable contact with the patient's face. For example, the air delivery conduit may be a textile conduit or a conduit including one or more portions with textile in its construction. Also, the conduit may include one or more portions constructed of other suitable materials, e.g., silicone, foam, etc.

Another aspect of the disclosed technology relates to an air delivery conduit having first and second conduit portions that cooperate to form a conduit, wherein each conduit portion includes an inner sealing layer and an outer textile layer.

Another aspect of the disclosed technology relates to a method of forming an air delivery conduit by blow molding at least one material to form a conduit.

Another aspect of the disclosed technology relates to an air delivery conduit including a tube having a plurality of anti-crush nodules disposed therein.

Another aspect of the disclosed technology relates to an air delivery conduit having a substrate (e.g., a rigid substrate) disposed inside the conduit for providing crush-resistance to the conduit.

Another aspect of the disclosed technology relates to a method of forming an air delivery conduit including enclosing a substrate (e.g., a rigid substrate) in the conduit to provide crush-resistance to the conduit.

Another aspect of the disclosed technology relates to an air delivery conduit including a conduit having an internal cavity for delivering pressurized air, and one or more particles disposed in the internal cavity for defining one or more passages.

Another aspect of the disclosed technology relates to an air delivery conduit including a tubular conduit constructed of spacer fabric and having one or more passages for conveying pressurized air.

Another aspect of the disclosed technology relates to a method of forming an air delivery conduit including forming a tubular conduit, and enclosing a spacer fabric in the conduit to provide crush-resistance to the conduit.

Another aspect of the disclosed technology relates to an air delivery conduit including a tubular conduit constructed of a warp knitted fabric having a high fabric density.

Another aspect of the disclosed technology relates to an air delivery conduit including a tubular conduit for delivering pressurized air and including at least one dividing wall separating the conduit into at least two air conveying channels.

Another aspect of the disclosed technology relates to a method of forming an air delivery conduit including a step of warp knitting a fabric into at least two adjoining tubular channels.

Another aspect of the disclosed technology relates to a mask assembly for treating sleep disordered breathing including an air delivery conduit according to any aspect of the disclosed technology.

Another aspect of the disclosed technology relates to a method of forming an air delivery tubular conduit comprising forming a support structure on or as part of a textile substrate, the support structure comprising one or more ribs or reinforcing members or portions, and forming the delivery tubular conduit using at least a portion of the textile substrate.

Other aspects, features, and advantages of the disclosed technology will become apparent from the following detailed description when taken in conjunction with the accompanying drawings, which are a part of this disclosure and which illustrate, by way of example, principles of the disclosed technology.

BRIEF DESCRIPTION OF THE DRAWINGS

The accompanying drawings facilitate an understanding of the various examples of the disclosed technology. In such drawings:

FIG. 38 is a cross-sectional view of an air delivery conduit according to an example of the disclosed technology;

FIG. 39 is an exploded view of the conduit of FIG. 38;

FIG. 40 is another exploded view of the conduit of FIG. 38;

FIG. 40-1 is a partial view of the substrate of FIG. 40 showing a cuff formed thereon according to an example of the disclosed technology;

FIG. 45 is a top view of the conduit of FIG. 44;

FIG. 46 is a side view of the conduit of FIG. 44;

FIG. 47 is a cross-sectional view taken along the line 47-47 of the conduit in FIG. 45;

FIG. 48 is a rear end view of the conduit of FIG. 44;

FIG. 50-1 is a partial side view of the substrate of the air delivery conduit of FIG. 44;

FIG. 50-2 is an end view of the substrate of the air delivery conduit of FIG. 44;

FIGS. 53-1 to 53-3 are cross-sectional views of an air delivery conduit and a method of making the air delivery conduit according to an example of the disclosed technology;

FIG. 77-1 shows a process of forming an air delivery conduit according to an example of the disclosed technology;

FIG. 77-1A is a partial perspective view of the air delivery conduit of FIG. 77-1;

FIG. 77-2 shows a process of forming an air delivery conduit according to an example of the disclosed technology;

FIG. 77-2A is a partial perspective view of the air delivery conduit of FIG. 77-2A;

FIG. 77-2B is a partial perspective view of an air delivery conduit according to another example of the disclosed technology;

FIG. 78-1 is a perspective view of a textile substrate according to an example of the disclosed technology;

FIG. 78-2 is a perspective view of a textile substrate according to an example of the disclosed technology;

FIG. 78-3 shows a process of forming a textile substrate into an air delivery conduit according to an example of the disclosed technology;

FIG. 78-4 is a perspective view of an air delivery conduit according to an example of the disclosed technology;

FIG. 78-5 is a perspective view of an air delivery conduit according to an example of the disclosed technology;

FIG. 79-1 is a partial perspective view of an air delivery conduit according to an example of the disclosed technology;

FIG. 79-2 is a partial perspective view of an air delivery conduit according to an example of the disclosed technology;

FIG. 80-1 shows a process of forming a support structure on a textile substrate according to an example of the disclosed technology;

FIG. 80-2 shows a process of forming a support structure on a textile substrate according to an example of the disclosed technology; and FIG. 80-3 shows a process of forming a textile substrate according to an example of the disclosed technology.

DETAILED DESCRIPTION OF ILLUSTRATED EXAMPLES

Figure 1:
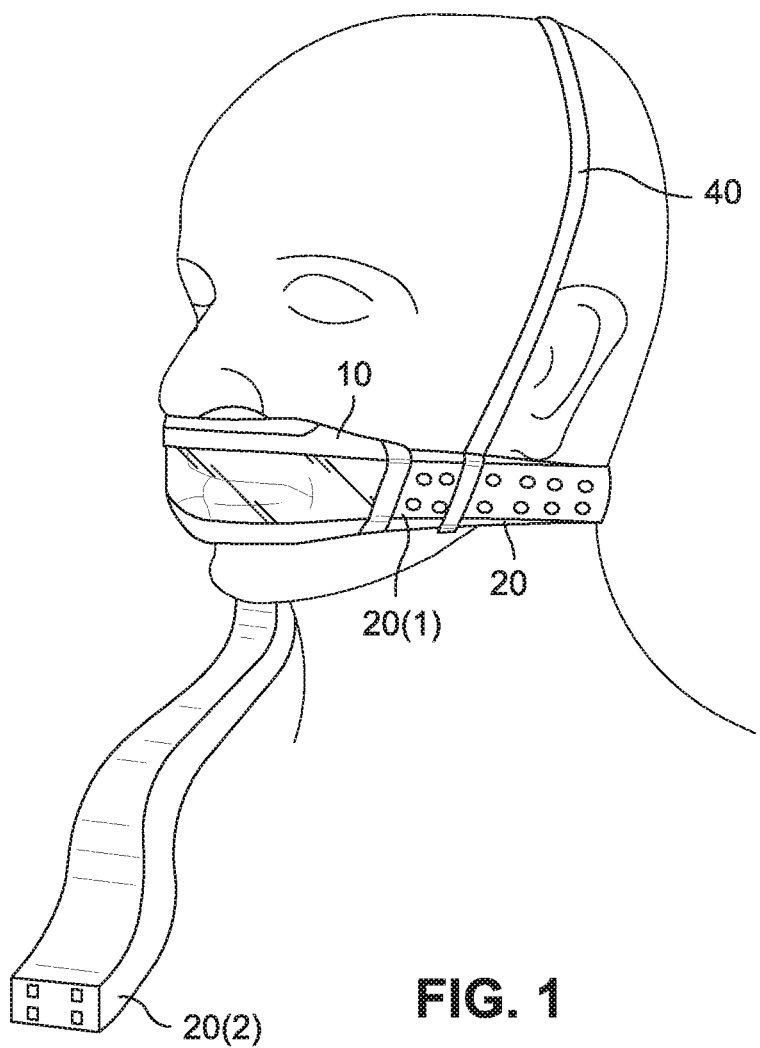
FIG. 1 is a perspective view of a patient interface including conduit headgear according to an example of the disclosed technology.

The following description is provided in relation to several examples (most of which are illustrated, some of which may not) which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

One or more examples may include exemplary dimensions. Although specific dimensions and ranges may be provided, it is to be understood that these dimensions and ranges are merely exemplary and other dimensions and ranges are possible depending on application. For example, ranges that vary from those provided +/−10% may be suitable for particular applications.

PAP System

A PAP system (e.g., CPAP system) typically includes a PAP device (including a blower for generating air at positive pressure), an air delivery conduit (also referred to as a tube or tubing), and a patient interface adapted to form a seal with the patient's face. In use, the PAP device generates a supply of pressurized air (e.g., 2-30 cm $H_2O$) that is delivered to the patient interface via the air delivery conduit. The patient interface or mask may have suitable configurations as is known in the art, e.g., full-face mask, nasal mask, oro-nasal mask, mouth mask, nasal prongs, nozzles, cradle, etc. Also, headgear may be utilized to comfortably support the patient interface in a desired position on the patient's face.

Conduit Headgear

Examples of the disclosed technology relate to an air delivery conduit in the form of conduit headgear structured to be worn on the patient's head in use and at least partially support the patient interface in a desired position on the patient's face in use. For example, one or more air delivery conduits may be communicated with the patient interface to deliver breathable gas to the patient interface and at least partially support the patient interface in position.

The air delivery conduit may be connected to a strap, the strap supporting or partially supporting the patient interface in a desired position on the patient's face in use.

Alternatively, the air delivery conduit may not be worn on the patient's head.

The one or more air delivery conduits may be routed along the patient's head in alternative manners. For example, the one or more air delivery conduits may be routed above the ears, below the ears, above and below the ears (multiple paths), or over the patient's nose/nasal bridge, between the patient's eyes, and over the patient's forehead. In an alternative form, the one or more air delivery conduits may be routed from the patient's airway and down over the chin towards the neck and chest of the patient.

The one or more air delivery conduits may have a diameter of 15 mm or less. The one or more air delivery conduits may have a diameter of 12 mm or less. The one or more air delivery conduits may have a diameter of 9 mm or less.

In an example, a single air delivery conduit may be communicated with the patient interface. For example, as shown in FIG. 1, a first end 20(1) of the conduit 20 may be adapted to engage an inlet of the patient interface 10 (e.g., nose (e.g. pillows) and mouth seal arrangement) and the second end 20(2) may be adapted to engage the outlet of a PAP device. As illustrated, the conduit 20 wraps around the patient's head so it extends along the patient's cheeks and under their ears to the back of their head. Also, a headgear strap 40 may pass over the patient's head and engage the conduit 20 to further support the patient interface and conduit in position.

Figure 2:
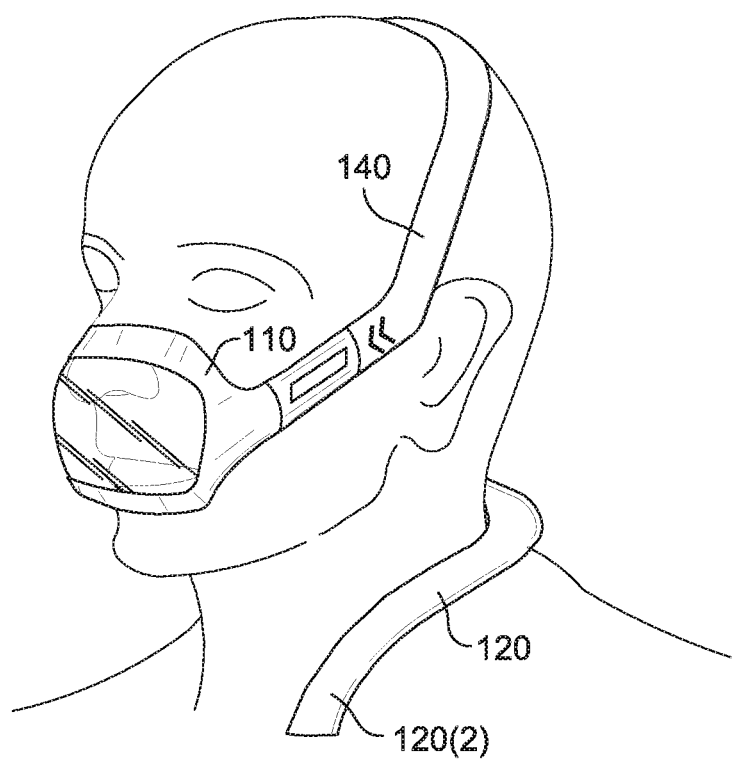
FIG. 2 is a perspective view of a patient interface including conduit headgear according to another example of the disclosed technology.

In FIG. 2, a first end of the conduit 120 may be adapted to engage an inlet of the patient interface 110 (e.g., nose and mouth mask) and the second end 120(2) may be adapted to engage the outlet of the PAP device. As illustrated, the conduit 120 may wrap around the patient's neck. Also, a headgear strap 140 may pass over the patient's head and engage respective sides of the patient interface 110 to further support the patient interface in position.

Figure 3:
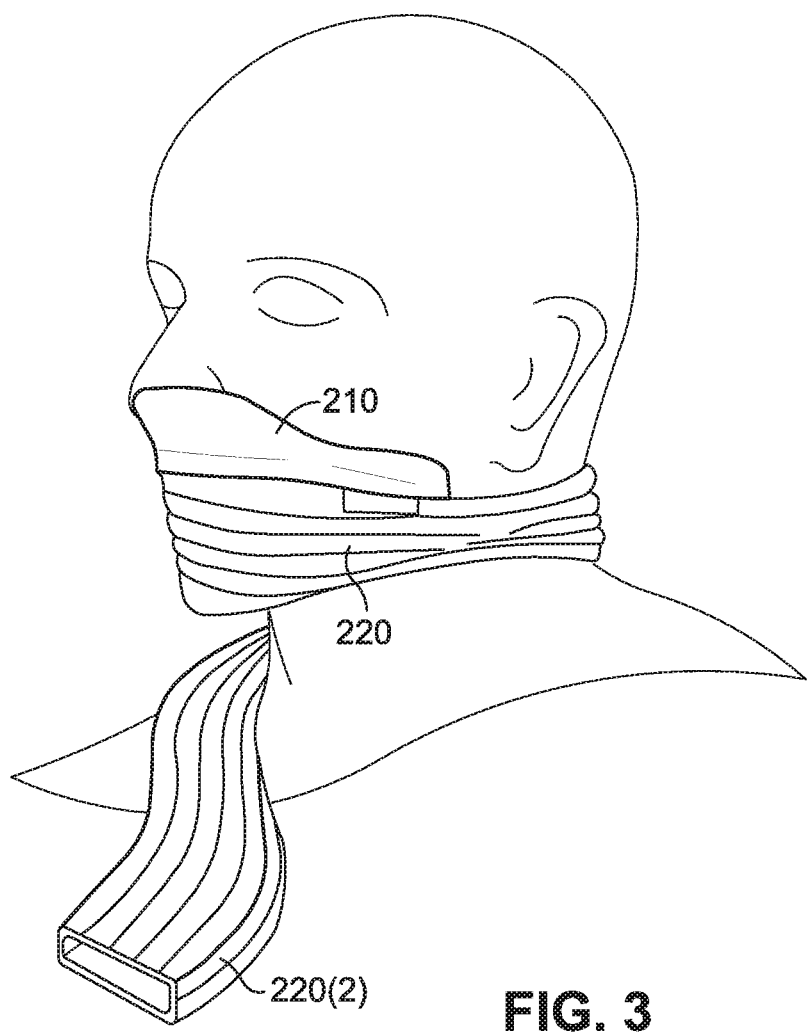
FIG. 3 is a perspective view of a patient interface including conduit headgear according to another example of the disclosed technology.

In FIG. 3, the conduit 220 wraps around the patient's head, below the ears and over the patient's mouth. The conduit 220 includes an end 220(2) adapted to engage the outlet of the PAP device. Also, the conduit 220 may be coupled or otherwise communicated with a patient interface 210 (e.g., nasal interface) to deliver gas to the patient interface. In an example, the portion of the conduit 220 covering the patient's mouth may include one or more openings to deliver gas to the patient's mouth. Alternatively, the portion of the conduit covering the patient's mouth may act as a mouth seal.

Figure 4:
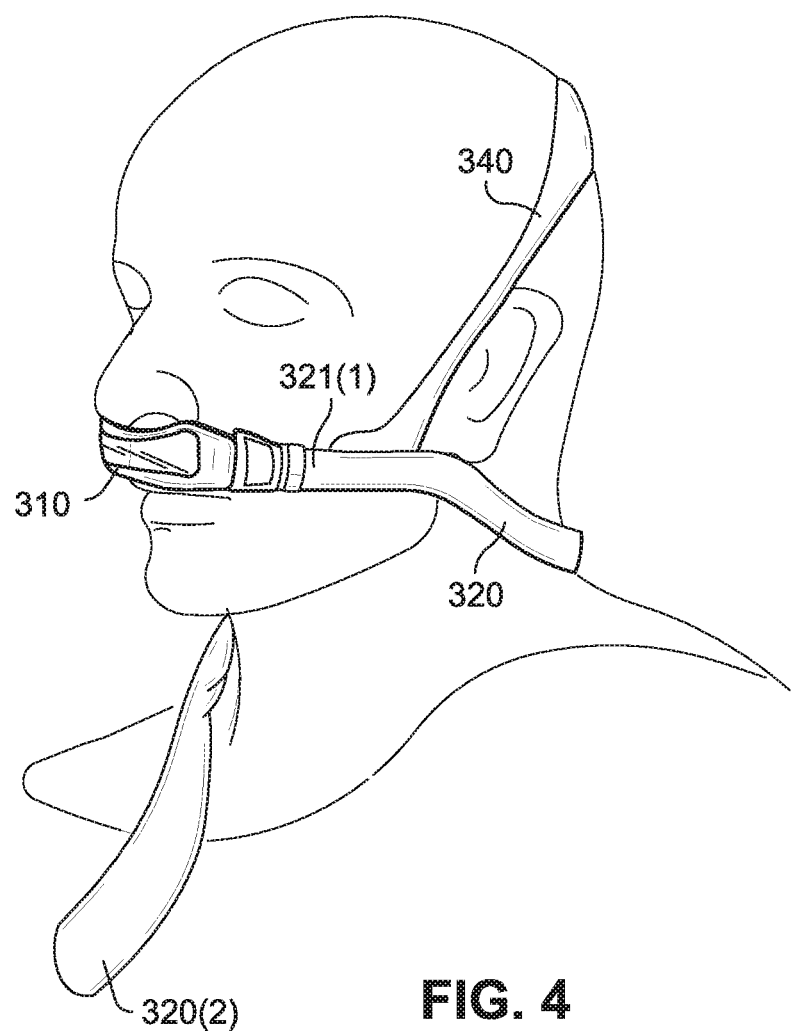
FIG. 4 is a perspective view of a patient interface including conduit headgear according to another example of the disclosed technology.

In FIG. 4, a first end 320(1) of the conduit 320 may be adapted to engage an inlet of the patient interface 310 (e.g., nasal prong/nozzle arrangement) and the second end 320(2) may be adapted to engage the outlet of the PAP device. As illustrated, the conduit wraps around the patient's head below the ears. Also, a headgear strap 340 may pass over the patient's head and engage the conduit to further support the patient interface and conduit in position.

Figure 5:
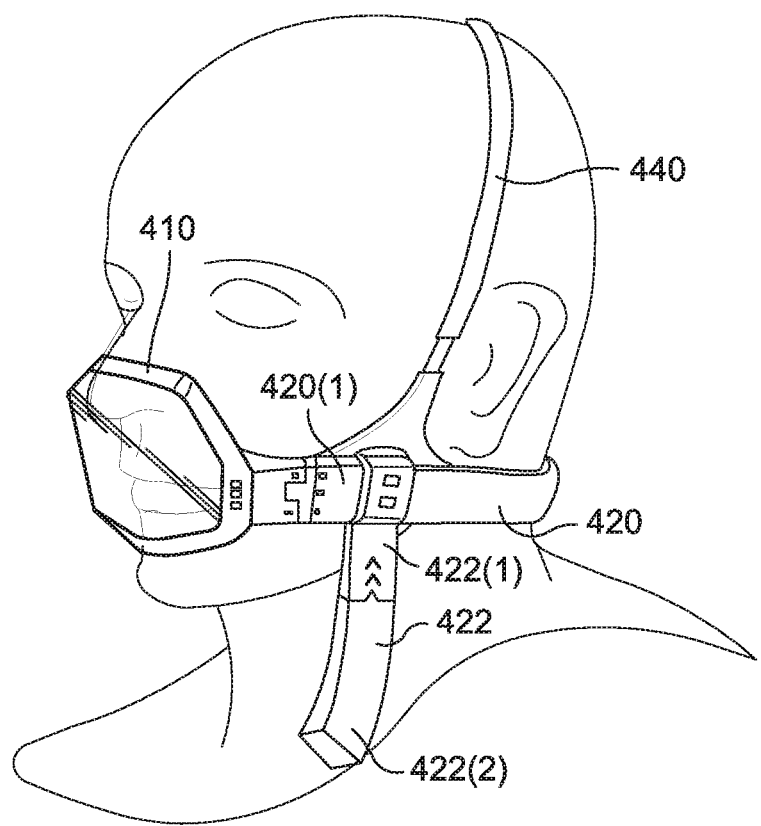
FIG. 5 is a perspective view of a patient interface including conduit headgear according to another example of the disclosed technology.

In FIG. 5, a first end 420(1) of the conduit 420 may be adapted to engage one side or inlet of the patient interface 410 (e.g., nose and mouth mask) and a second end of the conduit (not visible) may be adapted to engage the other side or inlet of the patient interface. The conduit 420 wraps around the patient's head so it extends along the patient's cheeks and under their ears to the back of their head. A second conduit 422 is communicated with the conduit 420 to deliver gas to the conduit and hence the patient interface, i.e., second conduit 422 includes a first end 422(1) adapted to engage the conduit 420 and a second end 422(2) adapted to engage the outlet of the PAP device. Also, a headgear strap 440 may pass over the patient's head and engage the conduit 420 to further support the patient interface and conduits in position.

Figure 6:
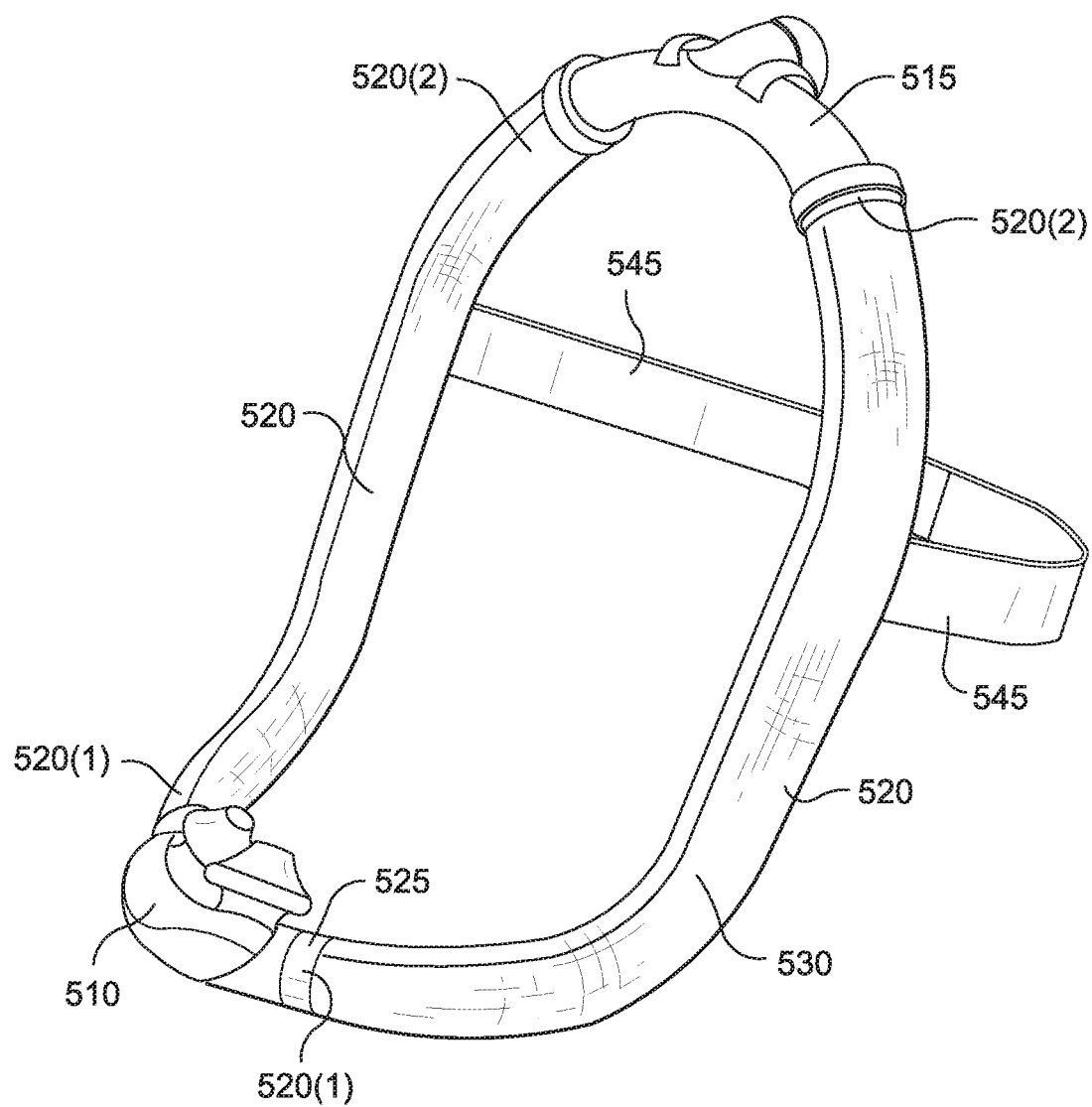
FIG. 6 is a perspective view of a patient interface including conduit headgear according to another example of the disclosed technology.

FIG. 6 shows an example of a pair of air delivery conduits communicated with the patient interface. As illustrated, a first cuff or end 520(1) of each conduit 520 may be adapted to engage a respective end or inlet of the patient interface 510 (e.g., nasal prong/nozzle arrangement) and the second cuff or end 520(2) may be adapted to engage a respective end of a manifold 515 communicated with the outlet of the PAP device via another air delivery conduit. In this example, each conduit 520 is adapted to extend from adjacent to or under the patient's nose, over the patient's cheeks, between the patient's eye and ear, and terminate at the crown of the patient's head.

In another example, a pair of air delivery conduits may be provided with each conduit directly connected to the PAP device, e.g., positioned on the patient's head in use. For example, the first end of each conduit may be adapted to engage a respective end or inlet of the patient interface and the second end may be adapted to engage a respective outlet of the PAP device.

In another example, the air delivery conduit may be structured to extend from the inlet of the patient interface, over the nose and between the patient's eyes, and to a manifold or PAP device positioned adjacent the crown of the patient's head.

In examples, the conduit(s) may be symmetrical on the patient's head (e.g., extend from both sides of the patient interface), or the conduit(s) may be asymmetrical on the patient's head (e.g., extending from only one side of the patient interface).

Also, while the air delivery conduit is described as being implemented into a CPAP system of the type described above, it may also be implemented into other tubing arrangements for conveying gas or liquid, such as ones associated with life support ventilation. That is, the CPAP system is merely exemplary, and aspects of the present technology may be incorporated into other suitable arrangements.

Conduit Materials and Properties

As noted above, examples of the disclosed technology relate to conduit headgear structured to be worn on the patient's head in use and at least partially support the patient interface in a desired position on the patient's face in use. As such, examples of the disclosed technology are directed towards air delivery conduits that are comfortable, occlusion resistant, kink resistant, and/or low cost. For example, the air delivery conduit may be sufficiently comfortable to lie on and adapted to provide a supply of air at pressure when a portion is being lain on by the patient.

Also, examples of the disclosed technology relate to air delivery conduits that include three-dimensional shaping to provide minimal assembly complexity, minimal possibility of occlusion by kink, and/or out-of-box intuitiveness (e.g., shape holding, easy to fit and adjust with little or no adjustment). For example, the air delivery conduit may include structural integrity or a self-holding form so it holds the conduit's shape, e.g., shape memory, whether the conduit is on or off the patient's head.

In addition, examples of the disclosed technology relate to air delivery conduits that are formed of one or more materials that provide intimate and comfortable contact with the patient's face. For example, the air delivery conduit may be a textile conduit or a conduit including one or more portions with textile in its construction. However, the conduit may include one or more portions constructed of other suitable materials, e.g., silicone, foam, etc.

Conduit Manufacturing Examples

The air delivery conduit may be manufactured in alternative manners.

For example, the air delivery conduit may be molded and then stripped from a long core, e.g., injection molding, LSR or compression molding.

In another example, the air delivery conduit may be blow molded.

In another example, the air delivery conduit may be dip molded, e.g., use silicone, polyurethane or synthetic polyisoprene.

In another example, the air delivery conduit may be formed using hydroformed thermoplastics.

In another example, the air delivery conduit may be formed by extrusion, e.g., silicone. In an example a continuous extrusion process may be used with hot air vulcanizing ovens to thermally cure the conduit.

In another example, the air delivery conduit may be formed by twisted extrusion.

In another example, the air delivery conduit may be formed using woven textile (e.g., surgical grafts). In an example, three-dimensional woven fabrics may be fabricated by modifying the conventional weaving mechanism. They may be produced in two methods which can also be used in conjunction dependant on the required outcome, e.g., the first method is to develop substantially thick fabrics through layering and the second method is to produce a fabric form by shedding and weft insertion horizontally and vertically. Advantages of three-dimensional weaving include: weaving into a three-dimensional shape or form; shape can be complex; and/or may include some form of lamination or support structure to maintain shape or air holding capability.

In another example, the air delivery conduit may be formed using spacer fabric. Spacer fabrics feature two complementary slabs of fabrics with a third layer tucked in between. The third or inner layer can take on a variety of shapes including tubes. The specific arrangement of the third layer can provide for a level of cushioning usually nonexistent in two dimensional fabrics. Advantages of spacer fabrics include: no lamination required if the spacer fabric is coated and/or has a secondary finish; pliable and flexible; can retain original shape; can build in air permeability; stability and/or stretch depending on materials chosen; and/or insulating.

In another example, the air delivery conduit may be formed as a knitted tube. Although commonly known as knitted or woven tubing, the correct term for seamless fabric tubing is circular or weft knit fabrics. Weft knitting uses one continuous yarn to form courses, or rows of loops, across a fabric. There are three fundamental stitches in weft knitting: plain-knit, purl and rib. On a machine, the individual yarn is fed to one or more needles at a time. Weft knitting machines can produce both flat and circular fabric. Circular machines produce mainly yardage but may also produce sweater bodies, pantyhose and socks. Advantages of knitted tubing include: the diameter can be varied along the length of the tube; and/or no seam to irritate the patient.

In another example, the air delivery conduit may be formed using bonded film bladders (e.g., TPU films, silicone films, welded, glued). Air bladders are manufactured primarily through the methods of die or ultrasonic cutting, thermoforming, and RF welding. Advantages of bonded film bladders include: can be formed into a three-dimensional shape; transparent materials available; and/or low cost.

In another example, the air delivery conduit may be formed using bonded film bladders (e.g., TPU films, silicone films, welded, glued) plus textiles. Air bladders are manufactured primarily through the methods of die or ultrasonic cutting, thermoforming, and RF welding. This method can be completed in conjunction with fabric lamination to produce polyurethane coated fabrics. Advantages of combining bonded film bladders and textiles include: can be formed into a three-dimensional shape; transparent materials available; low cost; and/or textile outer for comfort.

In another example, the air delivery conduit may be formed using films, e.g. polyurethane (PU), TPU, TPE, polypropylene or any other polymer substrate.

In another example, the air delivery conduit may be formed using coated fabrics. Coated fabrics consist of woven and non-woven cloth with a coating or resin applied to the surface or saturated into the bulk of the material to provide some additional property such as water or air impermeability. In an example, the cloth may be coated with silicone, parylene—these may have a very thin wall section.

In another example, the air delivery conduit may be formed using foam. Thermoforming is a method of processing flat material such as polyester or nylon into a finished three-dimensional shape. The process begins with fabric laminated to one or both sides of foam. The laminate is then placed in a two-piece mold to form the necessary shape. Heat and pressure are applied, permanently molding the laminate into the desired semi-rigid product. In an example, silicone or polyurethane may be used. An advantage of a foam air delivery includes no seam.

In another example, the air delivery conduit may be formed using thermoformed fabrics. Thermoformed fabrics differ in that they are fabrics which have been impregnated with stabilizing resins and a polymetric blend of duro and thermo plastics. It is these qualities rather than the deformation of an adhered laminate which allow thermoformed fabrics to assume their shape. In an example, the conduit could also be laminated. The fabric may be joined using thermal bonding or RF welding for example.

In another example, the air delivery conduit may be formed using non-woven fabrics. Non-woven fabric is a fabric-like material made from long fibers, bonded together by chemical, mechanical, heat or solvent treatment. The term is used in the textile manufacturing industry to denote fabrics, such as felt, which are neither woven nor knitted. Advantages of non-woven fabrics include: can be formed in a somewhat three-dimensional shape; may be air holding; and/or possible to have multiple lumens.

In another example, the air delivery conduit may be formed using braided tubing. Braided hoses are one of the most commonly used types of hoses on the market today. Braided hoses are considered versatile reinforced hoses, with different sizes and configurations of braided hoses being used around the home, in medical applications, manufacturing plants and in municipal utility systems. Advantages of braided tubing include: flexible but highly kink resistant; and/or can be shaped using heat.

In another example, the air delivery conduit may include heat shrink tubing.

Headgear Strap Examples

As noted above, one or more headgear straps may be provided to further support the patient interface and/or air delivery conduit(s) in position on the patient's head.

The one or more headgear straps may be manufactured in alternative manners.

For example, the one or more headgear straps may be thermoformed, ultrasonically die cut and welded.

In another example, the one or more headgear straps may be molded.

In another example, the one or more headgear straps may include ultrasonically die cut and welded stretch textile.

In another example, the one or more headgear straps may include three-dimensional woven textile (e.g., surgical grafts, high-performance sportswear).

In another example, the one or more headgear straps may include a combination of tubular woven textiles (e.g., socks, vascular grafts) and fabricated or thermoformed sections.

Patient Interface Examples

As noted above, the patient interface is adapted to form a seal with the patient's face. In an example, the patient interface includes a frame and a patient contacting portion (e.g., a cushion) adapted to contact the patient's face and form a seal or otherwise form an interface with the patient's face.

The patient contacting portion may be manufactured in alternative manners.

For example, one or more portions of the patient contacting portion may be constructed of textile.

In another example, one or more portions of the patient contacting portion may be constructed of textile over silicone.

In another example, one or more portions of the patient contacting portion may be constructed of textile over silicone and gel.

In another example, one or more portions of the patient contacting portion may be constructed of foam.

In another example, one or more portions of the patient contacting portion may be constructed of textile over foam.

In another example, one or more portions of the patient contacting portion may be constructed of foam over TPU/E, PU, polypropylene or other polymeric substrate. In such example, the patient contacting portion may be overmolded to the frame.

In another example, one or more portions of the patient contacting portion may be constructed of textile over TPU/E, PU, polypropylene or other polymeric substrate.

In another example, one or more portions of the patient contacting portion may be constructed of textile over a bladder.

In another example, one or more portions of the patient contacting portion may be constructed of three-dimensional woven textile.

In another example, one or more portions of the patient contacting portion may be constructed of silicone.

In another example, one or more portions of the patient contacting portion may be constructed of TPU/E, PU, polypropylene or other polymeric substrate.

Alternative Examples

In an alternative example, an inline muffler may be provided to the air delivery conduit, e.g., to eliminate or reduce conducted noise.

In an alternative example, one or more heatable elements may be incorporated into the air delivery conduit (e.g., heatable elements incorporated into a textile conduit) to create a humidified tube.

In an alternative example, one or more additives may be provided to the air delivery conduit, e.g., additives provided to textile conduit. Exemplary additives include additives that impart cool touch; anti microbial properties; and/or stain resistance.

In an alternative example, an exhalation resistor may be provided to the air delivery conduit, e.g., to boost therapy pressure on exhalation.

In an alternative example, the conduit may be structured as a heat exchanger. For example, a first conduit may transfer gases from the patient to an exhalation port. The exhaled gases may heat a copper wire. A second conduit may be positioned adjacent the first conduit with the copper wire positioned between the first and second conduit. The second conduit may transfer gases from a flow generator to the patient. The copper wire, having been heated from the exhaled gases, may then also heat the gases from the flow generator to the patient thereby warming the air for the patient to breathe in.

In a further example, the conduit may be provided with a filter. The filter may be constructed of a textile. The filter may be integrally formed with the conduit.

Air Delivery Conduit

The following provides alternative examples of an air delivery conduit.

1. Elastomer Conduit and Textile Cover

Figure 7:
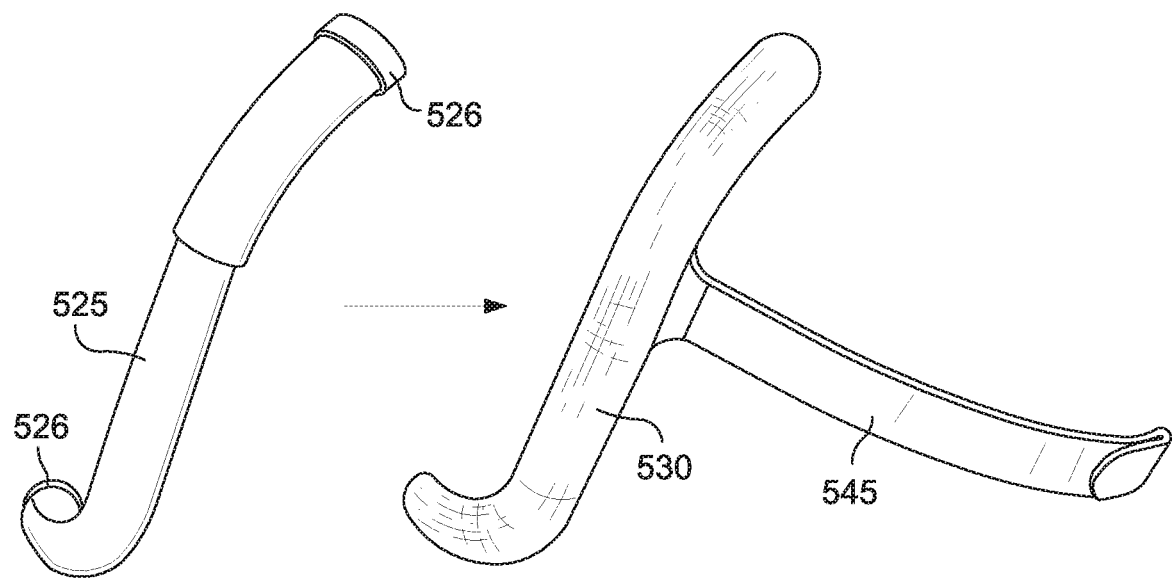
FIG. 7 is an exploded view of an air delivery conduit of FIG. 6.

FIGS. 6 and 7 show conduit headgear according to an example of the disclosed technology. In this example, each air delivery conduit 520 is in the form of a non-heated tube including a relatively soft three-dimensional elastomer conduit or tube 525 and a textile cover 530 that substantially encloses the elastomer tube 525. However, it should be appreciated that the conduit may be adapted for use as a heated tube.

The elastomer tube 525 may be formed by any of the manufacturing methods noted above, e.g., blow molding, film, extrusion. As illustrated, the elastomer tube is contoured or curved along its length to more closely follow a curvature of the patient's face in use and to orient and position ends of the tube for connection between the patient interface and manifold. For example, the tube is contoured to extend from adjacent to or under the patient's nose, over the patient's cheeks, between the patient's eye and ear, and terminate adjacent the crown of the patient's head.

The elastomer tube 525 may include a generally cylindrical or elliptical cross-sectional shape. However, other suitable cross-sectional shapes are possible, e.g., generally D-shaped cross-section. The cross-sectional shape of the elastomer tube 525 may at least partially determine the shape of the cover 530 that encloses the tube.

The wall thickness of the tube may be substantially constant or may vary along its length and/or may vary around its perimeter. For example, as shown in FIG. 7, one end portion of the tube 525 can be relatively thicker or wider than the remainder of the tube.

Also, each end of the tube 525 includes a cuff or thickened bead portion 526 to facilitate attachment of the conduit to the patient interface, manifold, etc.

The textile cover 530 may slide, wrap, and/or be otherwise positioned around the outside of the elastomer tube 525. The textile cover 530 may further comprise elements adapted to provide structural rigidity to the tube e.g. the textile cover 530 may comprise a reinforcing element such as a helix or ribbing.

As illustrated, a backstrap portion 545 extends from the cover 530 and is adapted to cooperate with the backstrap portion of the other air delivery conduit to form a back strap adapted to wrap around the back of the patient's head to support the patient interface in position (e.g., see FIG. 6). The back strap portions of the air delivery conduits may be releasably and adjustably connected to one another in any suitable manner, e.g., hook and loop material, ladder lock, etc. In an example, the back strap may assist in providing a sealing force for the patient interface.

The back strap portion 545 (e.g., constructed of textile) may be integrally formed in one piece with the textile cover 530. Alternatively, the back strap portion may be formed separately and attached to the cover by stitching, welding, or other suitable process. Also, the back strap portion may be formed separately and removably attached to the cover, e.g., the back strap portion may be looped through the cover.

2. Textile and Film Laminate

FIGS. 8 to 15 illustrate an air delivery conduit 620 according to another example of the disclosed technology. In this example, the air delivery conduit 620 includes first and second conduit portions 621, 622 that cooperate to form the conduit, i.e., first conduit portion provides a portion of the conduit circumference and the second conduit portion provides the remaining portion of the conduit circumference. In the illustrated example, the first and second conduit portions are symmetrical, however it should be appreciated that the conduit portions may be asymmetrical.

Each conduit portion 621, 622 includes an inner layer of a film laminate 650 that forms an interior surface of the conduit and an outer layer of a textile or fabric 655 that forms an exterior surface of the conduit. In an example, the film laminate is a polyurethane or medical grade film, and the textile is a thermoformable fabric.

Figures 13, 14:
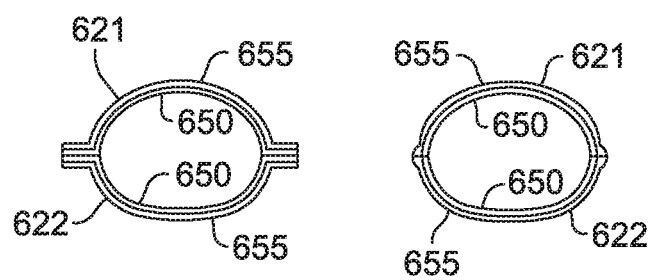
Figure 15:
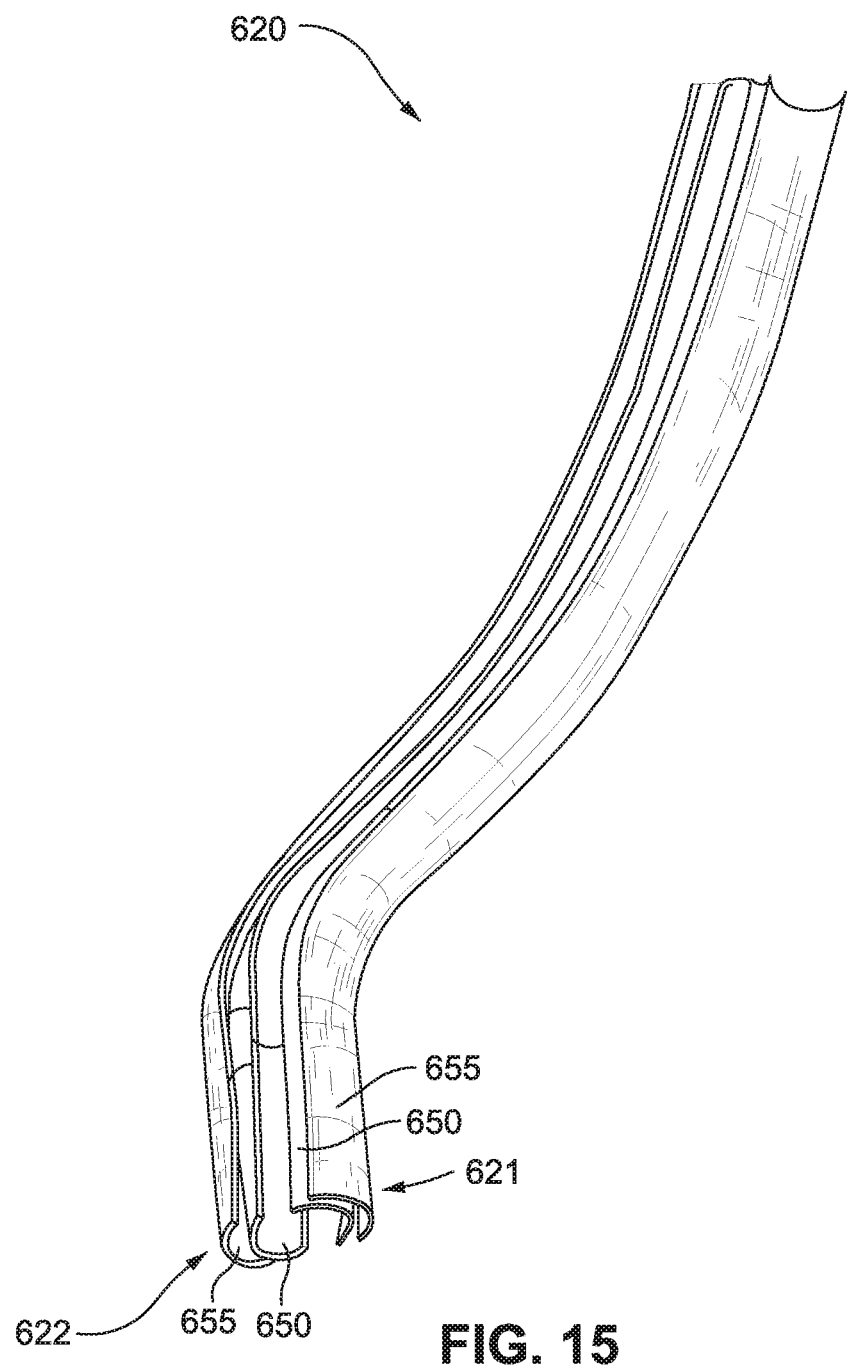
FIG. 15 another exploded view of the conduit of FIG. 8.
Figure 16:
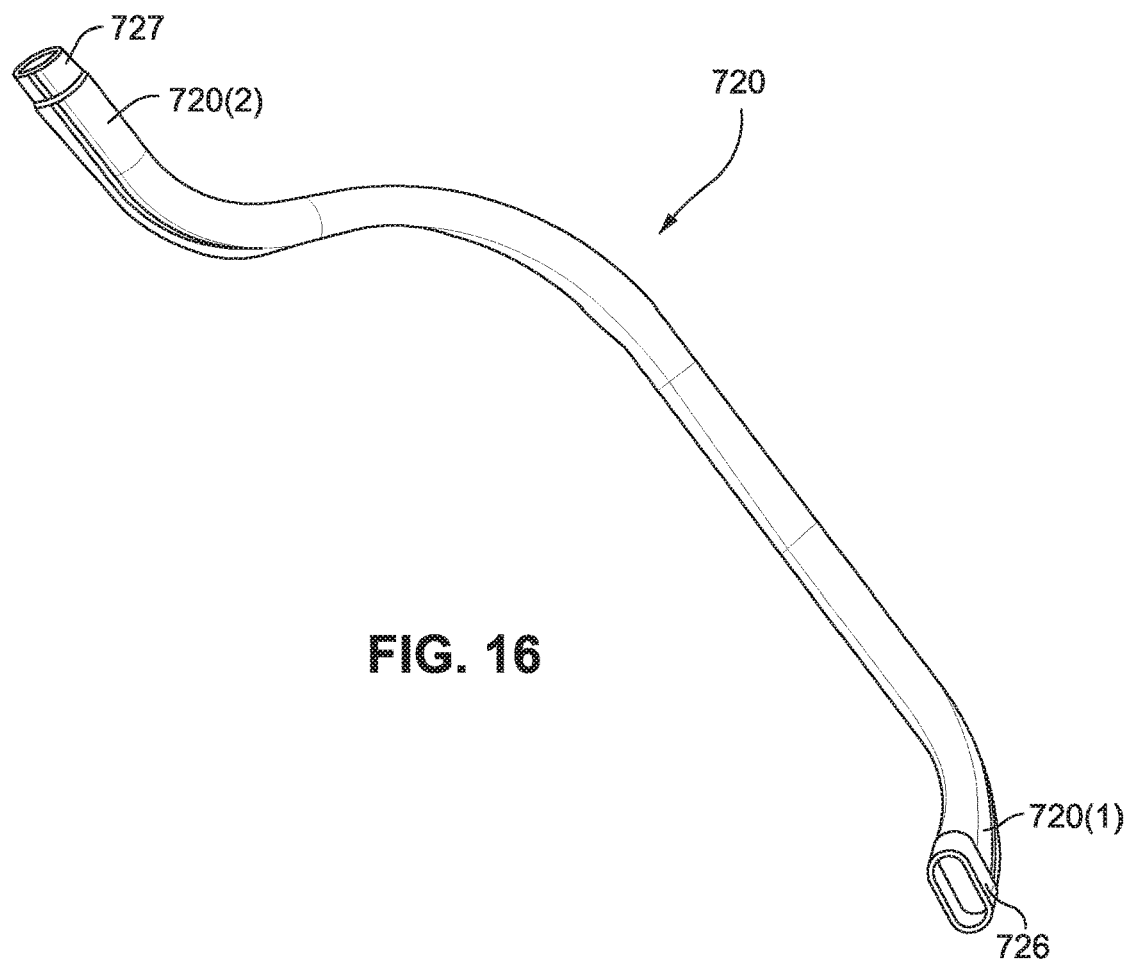
FIG. 16 is a perspective view of an air delivery conduit according to an example of the disclosed technology.
Figure 17:
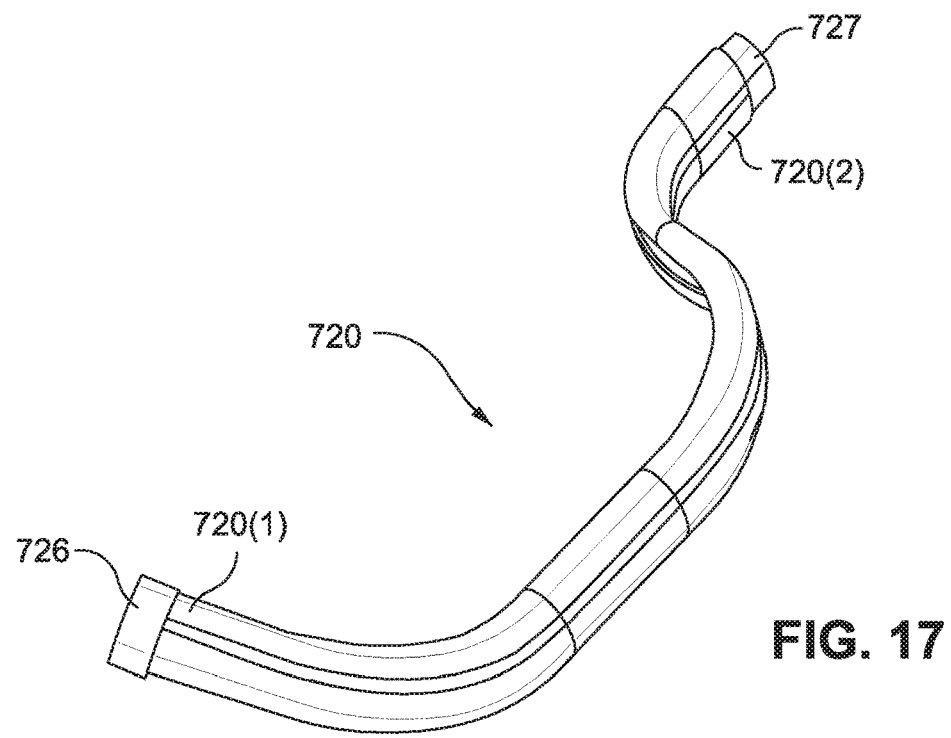
FIGS. 17 to 20 are alternative views of the conduit of FIG. 16.
Figure 18:
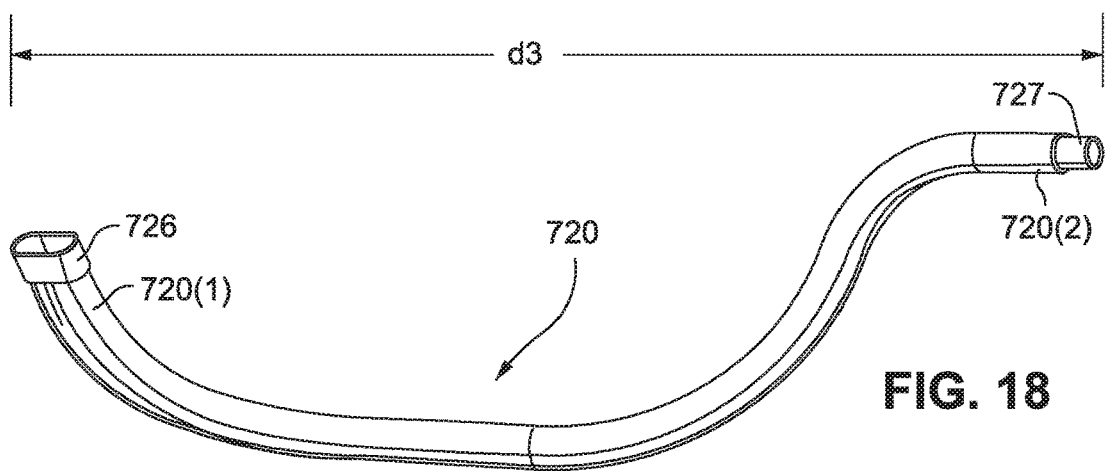
Figure 19:
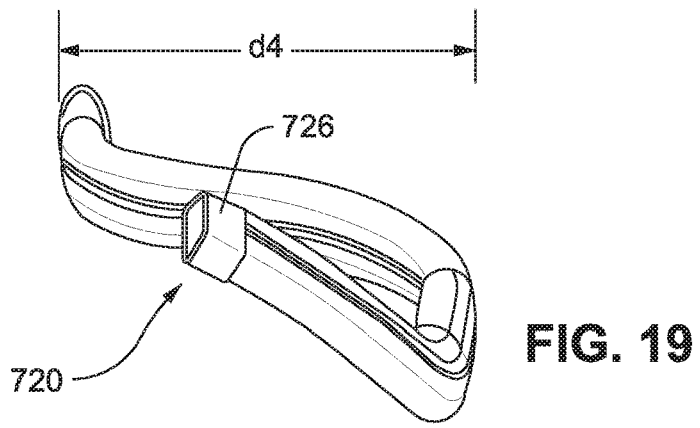
Figure 20:
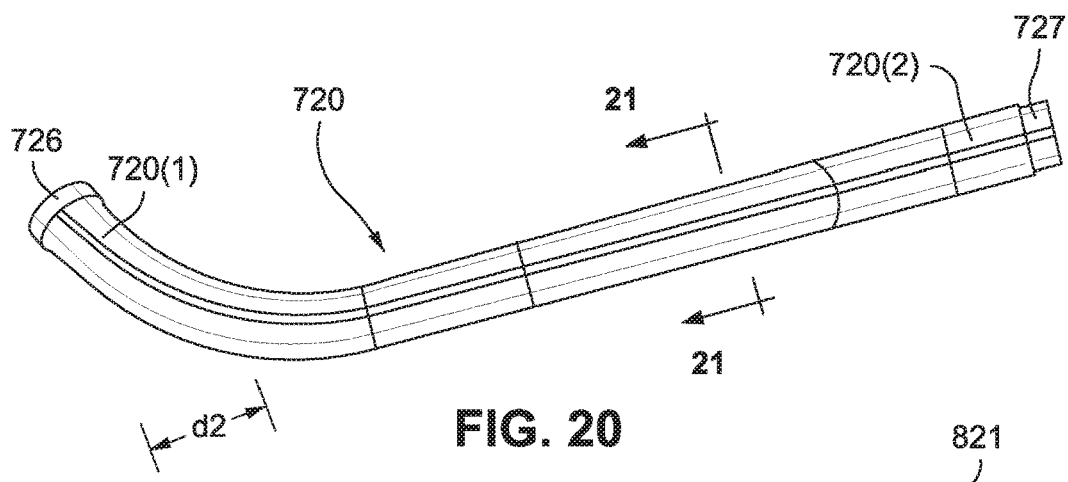

The film laminate 650 is applied to the fabric 655 (FIG. 11), and then the fabric and laminate are both thermoformed to create symmetrical complementary shapes (FIG. 12), i.e., conduit portions 621, 622. During the thermoforming process, the laminate adheres to the fabric giving it air impermeable properties. The two conduit portions 621 and 622 can then be seam welded as shown in FIG. 13 (e.g., RF weld to couple the conduit portions) and then ultrasonically die cut as shown in FIG. 14 (e.g., to remove seam edges) to create an air tight textile conduit. In use, such a conduit keeps its form in the absence of external force. However, the conduit is also collapsible and, when sufficient external force is applied, the conduit collapses. The form holding and collapsible features are particularly useful in the configuration shown in FIG. 6 which includes two conduits 520, one on each side of the patient's head. While both conduits maintain their form in the absence of external force, when the patient is lying in bed and turns to one side, the respective conduit conveniently collapses, thus improving patient comfort. The remaining conduit maintains the air supply to the patient interface 510. The conduit may also be air impermeable.

Figure 8:
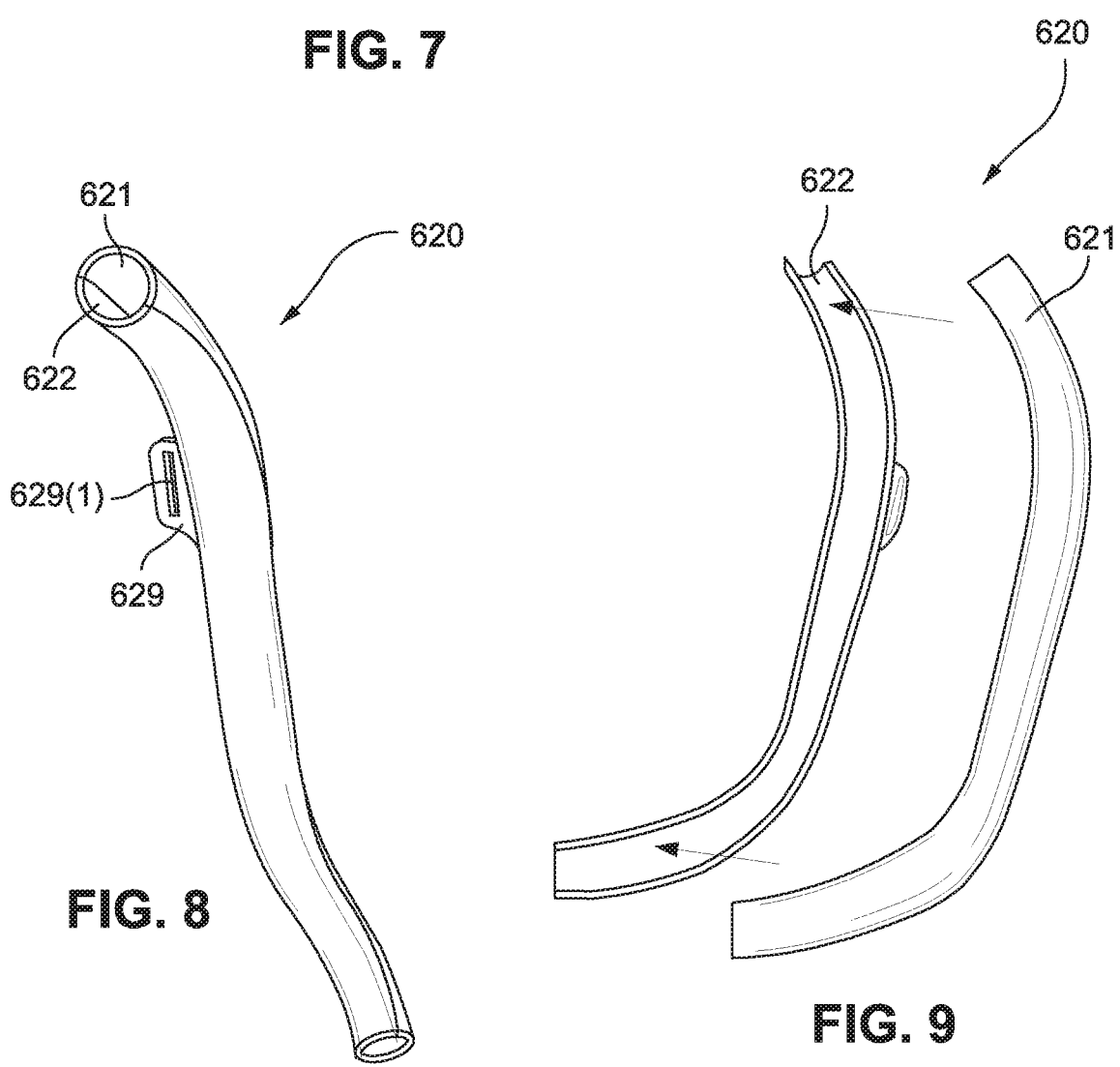
FIG. 8 is a perspective view of an air delivery conduit according to an example of the disclosed technology.
Figure 9:
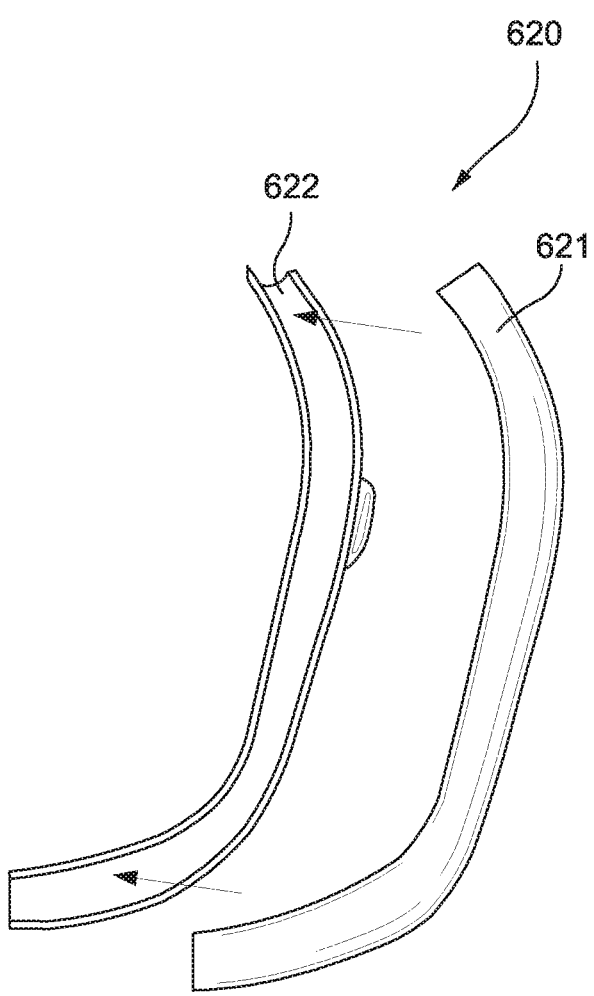
FIG. 9 is an exploded view of the conduit of FIG. 8.
Figure 10:
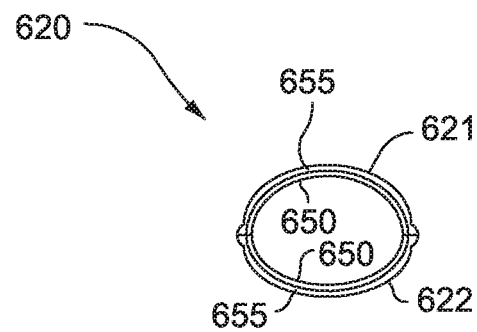
FIG. 10 is a cross-sectional view of the conduit of FIG. 8.
Figures 11, 12:
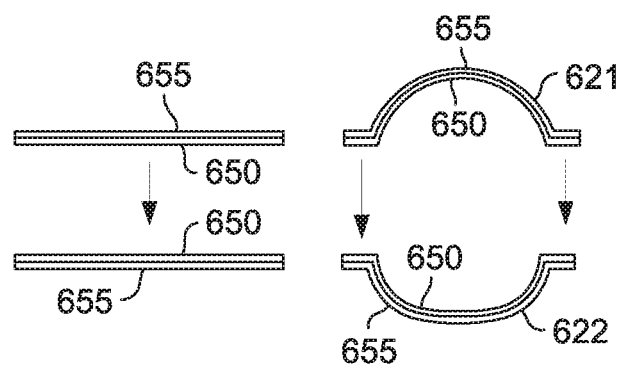
FIGS. 11 to 14 illustrate exemplary steps for manufacturing the conduit of FIG. 8 according to an example of the disclosed technology.

In an example, as shown in FIG. 8, the air delivery conduit may include a tab portion 629 providing a slot 629(1) to allow attachment of a back strap.

In a further alternative, the textile or fabric may be sealed by means other than a film laminate. For example, the textile or fabric may be sealed by spraying on a polymeric substance, such as silicone, or a powder that is then heated to congeal and create an impermeable barrier.

3. Blow Molded

FIGS. 16 to 21 illustrate an air delivery conduit 720 according to another example of the disclosed technology. In this example, the air delivery conduit 720 is formed by blow molding to form a conduit that is contoured or curved along its length to more closely follow a curvature of the patient's face in use and to orient and position ends of the conduit for connection, e.g., between a patient interface and a manifold. In blow molding, material is extruded into a mold, and then air is pushed through the material to create the conduit.

As illustrated, one end 720(1) of the conduit 720 includes a cuff or thickened bead portion 726 and the opposite end 720(2) includes a portion 727 of reduced thickness, e.g., to facilitate attachment of the ends to the patient interface, manifold, etc.

Figure 21:
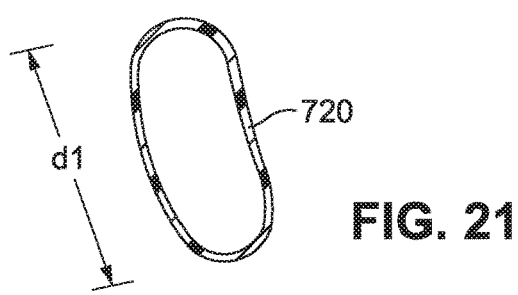
FIG. 21 is a cross-sectional view of the conduit of FIG. 16.

As shown in FIG. 21, the conduit 720 includes a generally elliptical cross-sectional shape. However, other suitable cross-sectional shapes are possible, e.g., cylindrical, generally D-shaped cross-section. In an example, as shown in FIG. 21, d1 along the major axis is about 15-25 mm, e.g., 18.9 mm or 19 mm, and d2 along the minor axis is about 5-15 mm, e.g., 9.4 mm or 9 mm.

In an example, the overall length of the tube d3 (FIG. 18) is about 250-300 mm, e.g., 284 mm, and the overall width of the tube d4 (FIG. 19) is about 50-100 mm, e.g., 87 mm.

Figure 22:
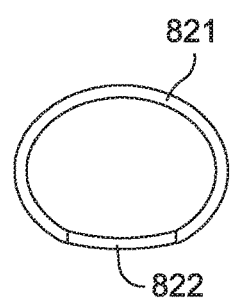
FIG. 22 is a cross-sectional view of the conduit of FIG. 16 according to an alternative example of the disclosed technology.

In an example, multiple materials or a similar material with different hardnesses may be extruded to achieve varying stiffness of the conduit. For example, as shown in FIG. 22, the conduit includes a first portion 821 of the conduit circumference constructed of a softer material (e.g., 50-60 Shore A hardness) and a second portion 822 of the conduit circumference constructed of a harder material (e.g., 80 or more Shore A hardness). However, it should be appreciated that the conduit circumference may be divided into any suitable number of harder/softer portions in any suitable arrangement.

The positioning of the portions along the circumference as well as the relative size of the portions may vary, e.g., depending on application and/or patient comfort. For example, the harder material may be positioned on a patient contacting side of the conduit to maintain the shape of the conduit. Alternatively, the harder material may be positioned on the non-patient contacting side of the conduit to aid in comfort.

4. Crush Resistant Film and Fabric Thermoform

Figure 23:
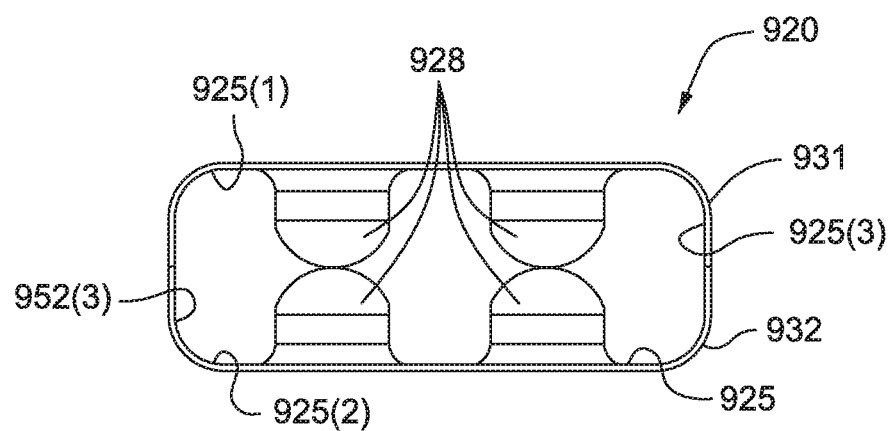
FIG. 23 is a cross-sectional view of an air delivery conduit according to an example of the disclosed technology.
Figure 24:
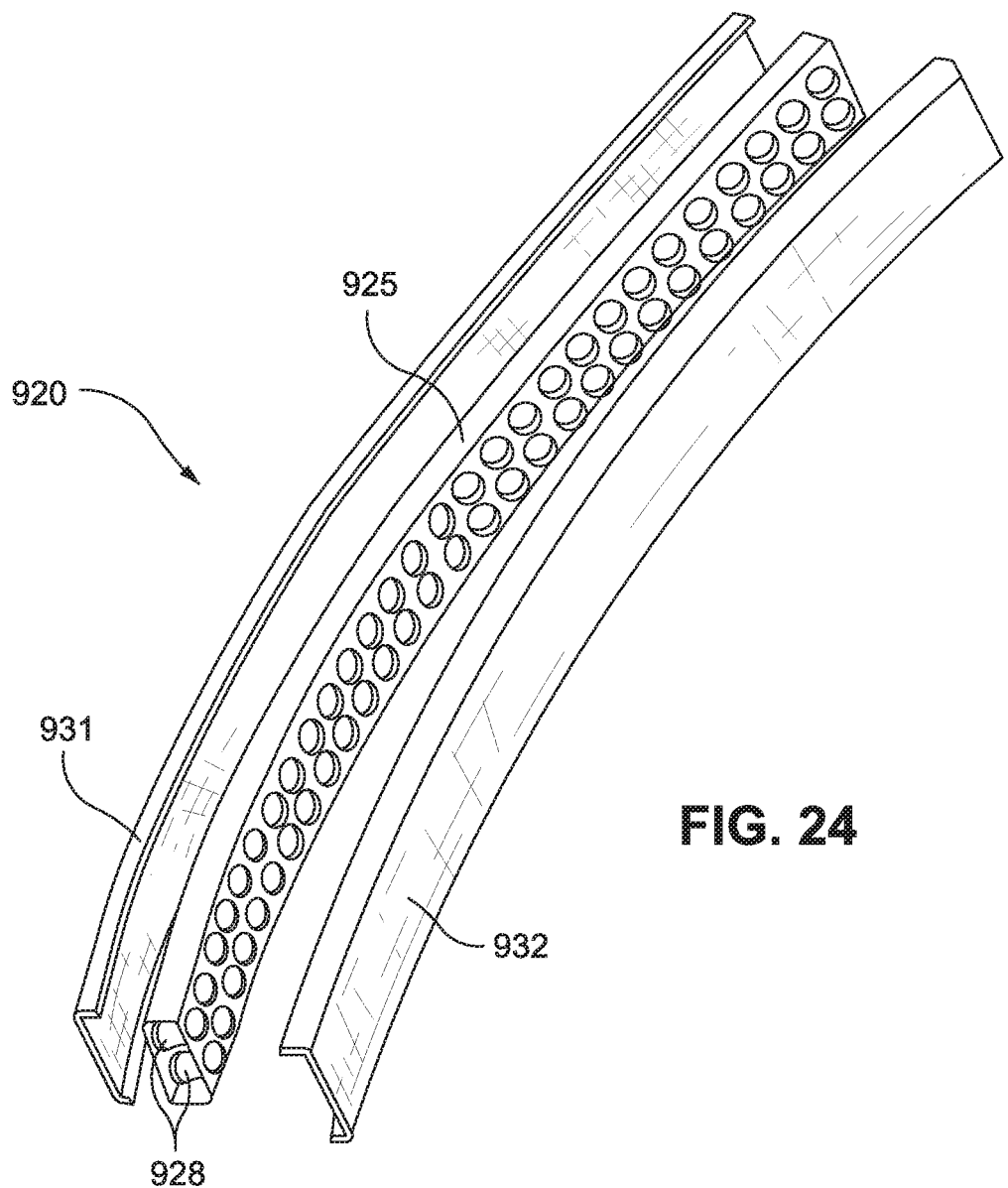
FIG. 24 is an exploded view of the conduit of FIG. 23.
Figure 25:
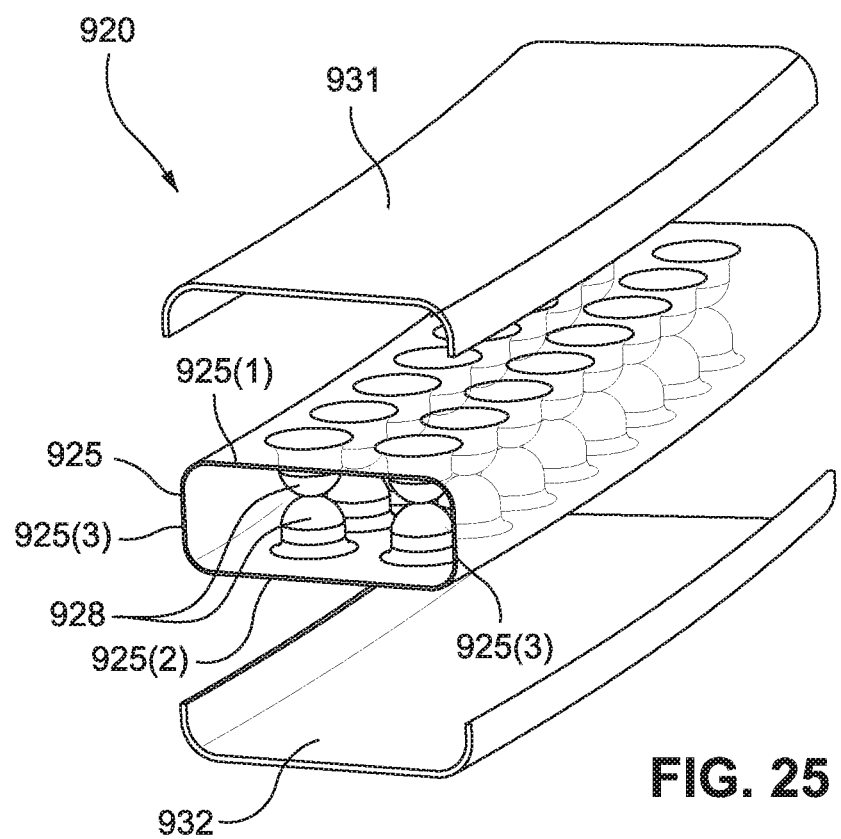
FIG. 25 is another exploded view of the conduit of FIG. 23.

FIGS. 23 to 25 illustrate an air delivery conduit 920 according to another example of the disclosed technology. In this example, the air delivery conduit 920 includes a tube 925 and textile cover portions 931, 932 that substantially enclose the tube 925. The textile cover portions 931, 932 may be formed separately to the tube 925 and slipped, wrapped or otherwise attached to the tube 925. The tube and/or nodules may be made from one or a combination of elastomers such as polyurethane, thermoplastic elastomers, or other material that is preferably able to be welded and/or blow molded. The textile cover portions 931, 932 may alternatively be formed with the tube 925 prior to the tube 925 being thermoformed into shape. For example, a textile may be laminated, coated or otherwise formed with a polymeric substance to form a composite material. This composite material may then be thermoformed or otherwise formed to create the nodules as described below.

The tube 925 is a thermoformed tube having a flat or non-cylindrical cross-section with anti-crush or occlusion resistant nodules or ribs 928 to provide crush resistance to the tube. The nodules may be shaped to decrease air resistance or impedance in the tube.

In FIGS. 23 to 25, the tube 925 is generally rectangular including an upper wall 925(1) with two downwardly extending nodules 928, a lower wall 925(2) with two upwardly extending nodules 928, and opposing side walls 925(3) connecting the upper and lower walls. As illustrated, the downwardly and upwardly extending nodules are aligned and engaged with one another. Each nodule includes rounded edges, e.g., to decrease air resistance. It should be appreciated that the tube may include any suitable number of nodules (e.g., one, two, three, or more) along the upper wall and lower wall, and the nodules may be aligned and/or offset from one another. In addition, the nodules may include other suitable shapes and may be arranged along the upper and/or lower walls in other suitable manners, e.g., symmetrically and/or asymmetrically arranged. Alternatively, only one of the walls may provide one or more nodules adapted to engage the other of the walls.

Figure 26:
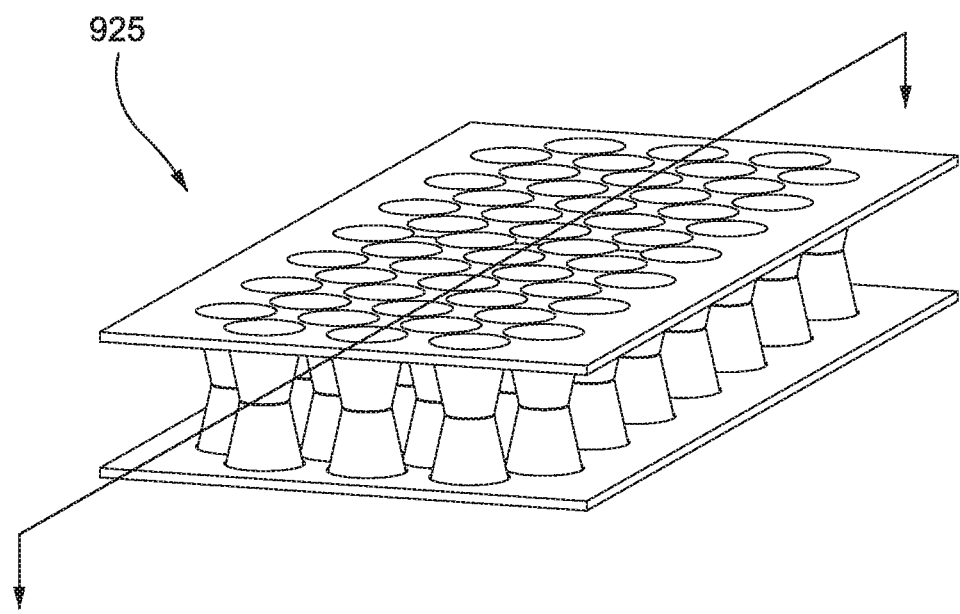
FIG. 26 is a perspective view of a tube for the conduit of FIG. 23 according to an alternative example of the disclosed technology.
Figure 28:
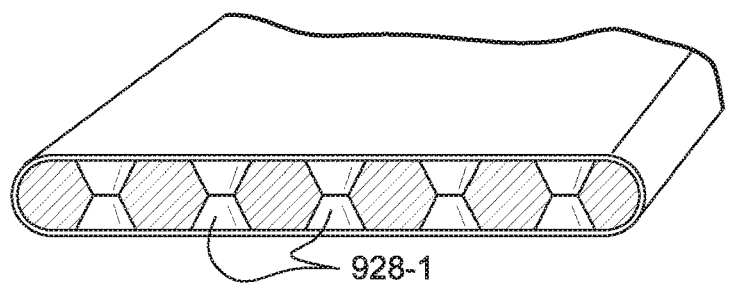
FIGS. 28 to 31 show tubes for the conduit of FIG. 23 with nodules according to alternative examples of the disclosed technology.
Figure 29:
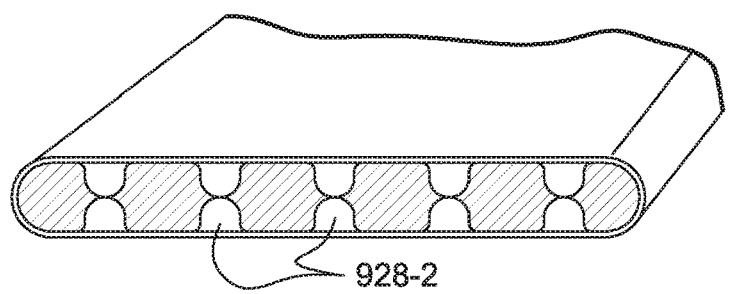
Figure 30:
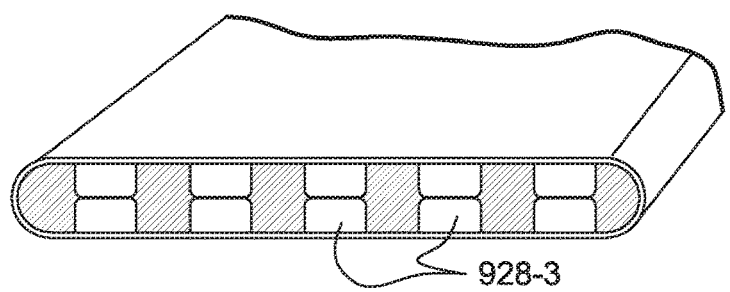
Figure 31:
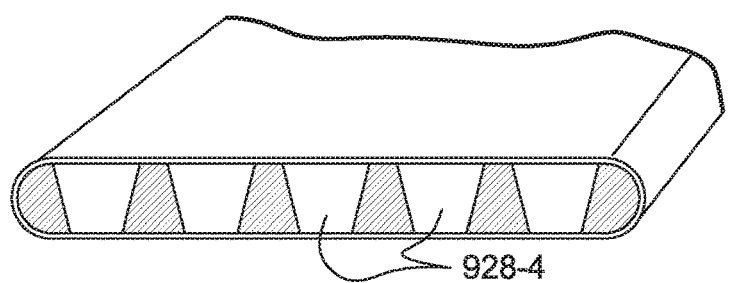

FIGS. 28 to 31 show alternative configurations of the nodules, e.g., though the section line shown in FIG. 26. In FIG. 28, each nodule 928-1 includes a generally frusto-conical configuration. In FIG. 29, each nodule 928-2 is in the form of a rounded protuberance. In FIG. 30, each nodule 928-3 includes a box-like configuration. In FIG. 31, each nodule 928-4 includes a generally frusto-conical configuration, and only a single nodule is provided between the upper and lower walls, i.e., nodule only extends from one of the walls towards the other of the walls.

Figure 27:
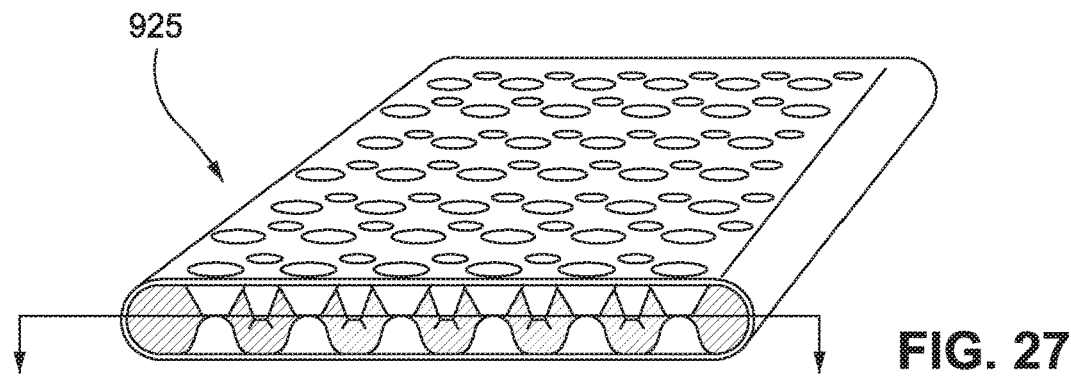
FIG. 27 is a perspective view of a tube for the conduit of FIG. 23 according to an alternative example of the disclosed technology.
Figure 32:
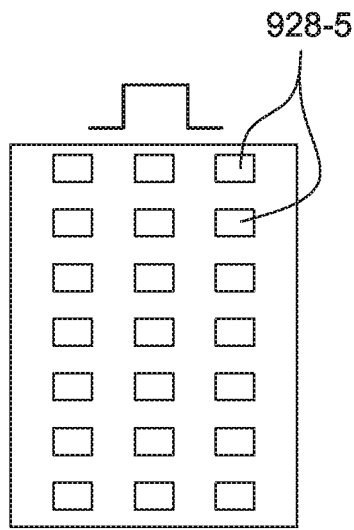
FIGS. 32 to 37 show tubes for the conduit of FIG. 23 with nodule arrangements according to alternative examples of the disclosed technology.
Figure 33:
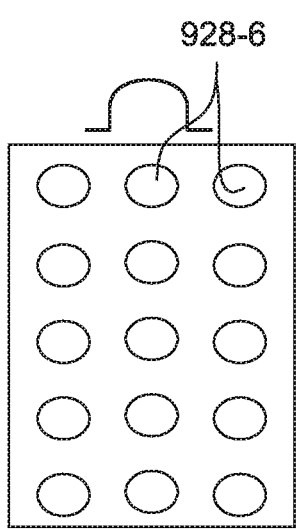
Figure 34:
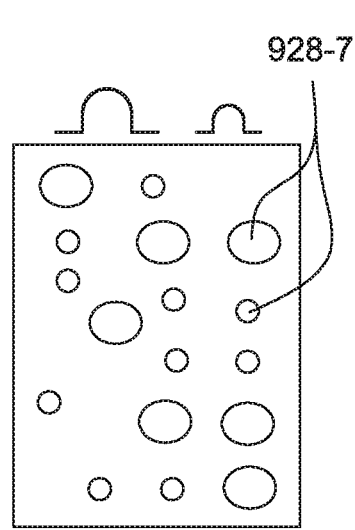
Figure 35:
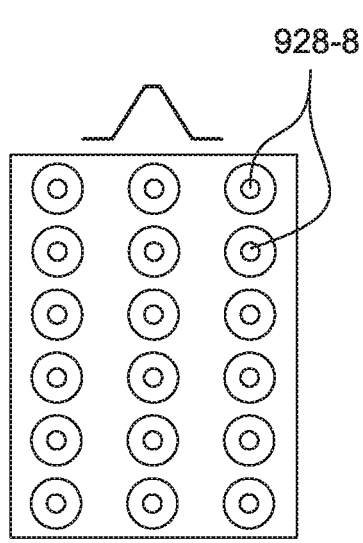
Figure 36:
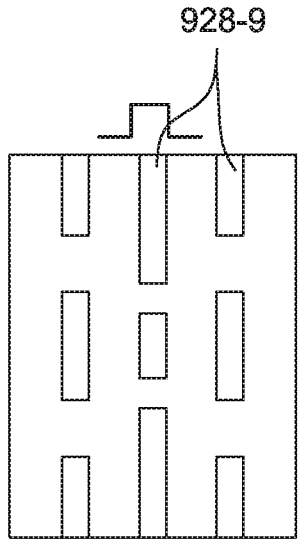
Figure 37:
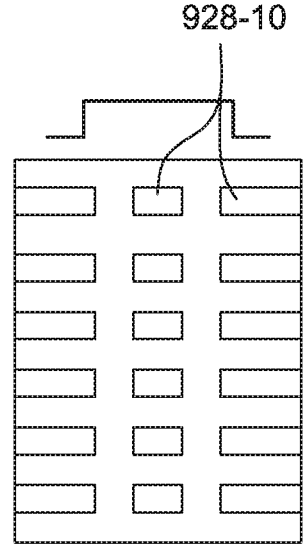

FIGS. 32 to 37 illustrate alternative configurations of the nodule arrangement along a length of the tube, e.g., through the section plane shown in FIG. 27. In FIG. 32, the nodule arrangement includes box-like nodules 928-5 aligned in rows and columns along the length of the tube. In FIG. 33, the nodule arrangement includes cylindrical or elliptical nodules 928-6 aligned in rows and columns along the length of the tube. In FIG. 34, the nodule arrangement includes cylindrical and/or elliptical nodules 928-7 of different sizes arranged irregularly along the length of the tube. In FIG. 35, the nodule arrangement includes generally frusto-conical nodules 928-8 aligned in rows and columns along the length of the tube. In FIG. 36, the nodule arrangement includes rectangular nodules 928-9 of different sizes arranged to extend parallel to the longitudinal axis of the tube. In FIG. 37, the nodule arrangement includes rectangular nodules 928-10 of different sizes arranged to extend transverse to the longitudinal axis of the tube.

Referring back to FIG. 25, first and second textile cover portions 931, 932 cooperate to form a cover for the tube 925, i.e., first textile cover portion provides a cover for a portion of the tube circumference and the second textile cover portion provides a cover for the remaining portion of the tube circumference. The textile cover portions may be constructed of a laminated fabric (e.g., TPE, TPU) each of which may be thermoformed to create its shape and then the textile cover portions may be seam welded to couple the textile cover portions.

Such conduit 920 is occlusion resistant (due to the nodules providing structural support to the tube passage), air impermeable, and form holding in use.

5. Substrate Reinforced Film and Fabric Thermoform

FIGS. 38 to 40 illustrate an air delivery conduit 1020 according to another example of the disclosed technology. Similar to the conduit described above, the air delivery conduit 1020 includes first and second conduit portions 1021, 1022 that cooperate to form the conduit, and each conduit portion 1021, 1022 includes an inner layer of a film laminate 1050 (e.g., polyurethane or medical grade film) and an outer layer of a textile or fabric 1055 (e.g., synthetic or specified fabric). The film laminate is applied to the fabric, the fabric and laminate are both thermoformed to create symmetrical shapes, i.e., a conduit portion, and then two of the conduit portions are seam welded (e.g., RF weld to couple the conduit portions) and then ultrasonically die cut (e.g., to remove seam edges) to create an air tight textile conduit.

Moreover, a rigid substrate, or semi-rigid substrate (including for example polypropylene, nylon), structure, support, or preform 1060 is inserted into the conduit (i.e., post RF welding/fabric joining) in order to provide crush resistance and form. The substrate 1060 also provides an opportunity for the integration of cuffs and fittings in the substrate, e.g., mold a patient interface connector (e.g., cuff 1060(1)) or clip to an end of the rigid substrate, as shown in FIG. 40-1.

Figure 41:
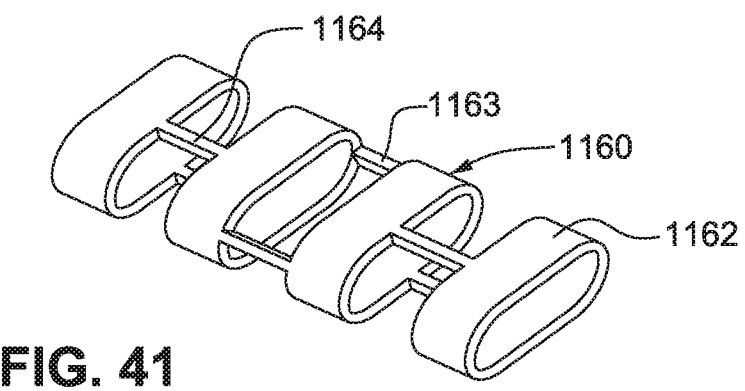
FIGS. 41 and 42 are perspective views of substrates for the conduit of FIG. 38 according to alternative examples of the disclosed technology.

In the illustrated example, as best shown in FIG. 38, the substrate 1060 includes a central base 1062 and upper and lower generally curved arms 1063, 1064 extending from respective sides of the base. In another example, as shown in FIG. 41, a substrate 1160 includes a series of body portions 1162 connected by alternating sets of lateral links 1163 and central links 1164. The alternating links 1163,1164 are designed to provide structural support to the substrate 1160 in both the horizontal and vertical directions, while at the same time providing flexibility.

Figure 42:
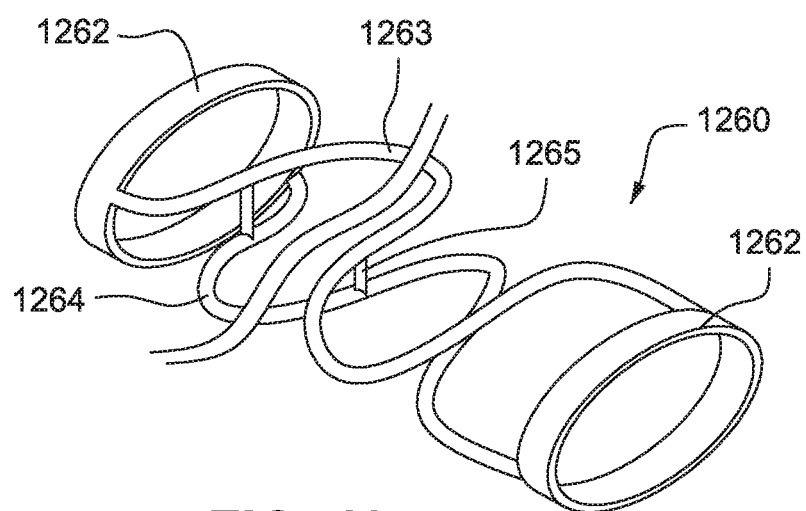
Figure 43:
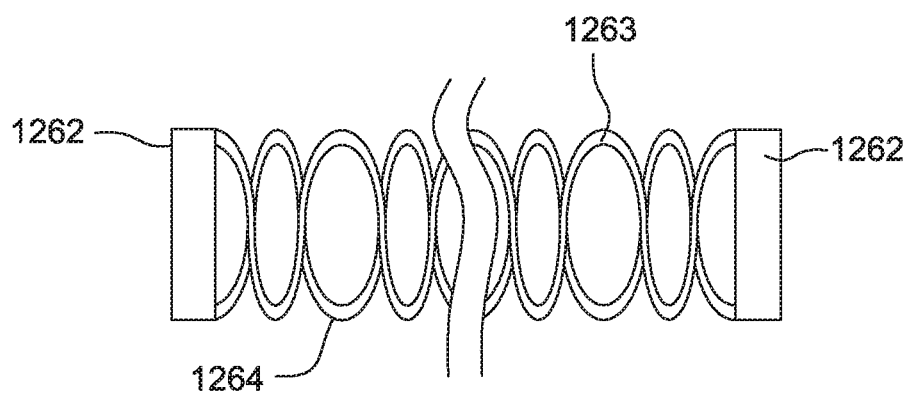
FIG. 43 is a top view of the substrate of FIG. 42.
Figure 44:
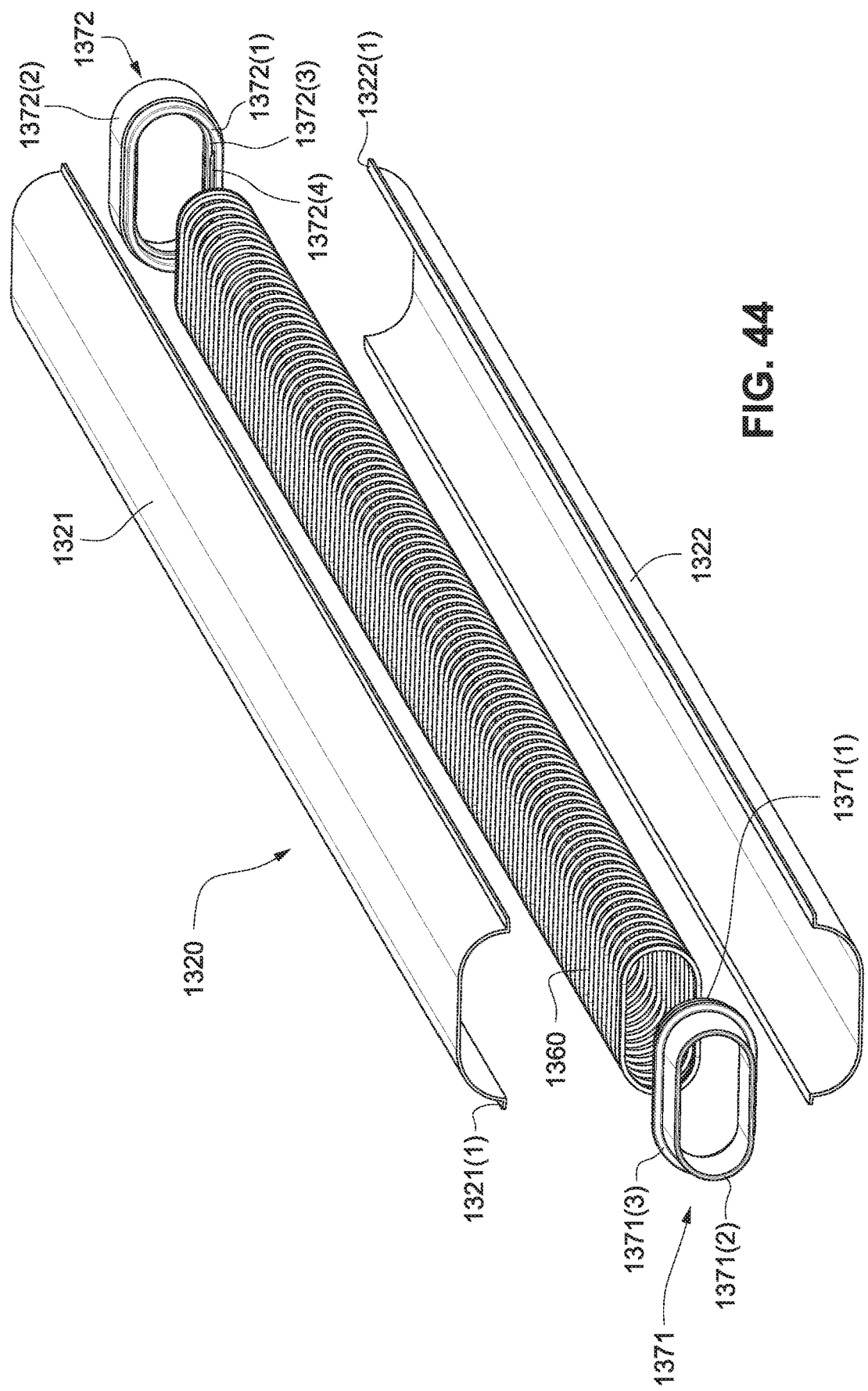
FIG. 44 is an exploded view of an air delivery conduit according to an example of the disclosed technology.

In yet another example shown in FIGS. 42 and 43, a substrate 1260 includes two support members 1262 connected by a first wave member 1263 and a second wave member 1264. The first and second wave members have a matching or mirror image sinusoidal shape and are connected to each support member 1262 at opposite points so as to provide a space between the wave members 1263,1264 that will function as an air passageway. The wave members 1263,1264 are described as having an identical shape; however, one skilled in the art would recognize that the wave members could have different shapes while still managing to provide an air delivery conduit that is crush-resistant and suitable for delivering pressurized gas. Any suitable number of wave members could also be connected between the support members 1262. Intermediate support members 1262 could also be provided.

A plurality of struts 1265 may extend between and connect the first 1263 and second 1264 wave members to provide structural support.

The substrate may have other suitable arrangements to provide crush resistance and form. Such conduit 1020 is air impermeable, form holding, and allows two-dimensional material processing.

FIGS. 44 to 50-2 illustrate an air delivery conduit 1320 according to another example of the disclosed technology. Similar to the conduit described above with regard to FIG. 38, the air delivery conduit 1320 includes first and second conduit portions 1321, 1322 that are welded (e.g., RF welded) together to form the conduit. The conduit portions could have flanges 1321(1),1322(1) on opposite sides to provide weld points. The conduit portions may further be ultrasonically die cut (e.g., to remove seam edges). Each conduit portion 1321, 1322 includes an inner layer of a film laminate (e.g., polyurethane or medical grade film) and an outer layer of a textile or fabric (e.g., synthetic or specified fabric).

Figures 1, 50:
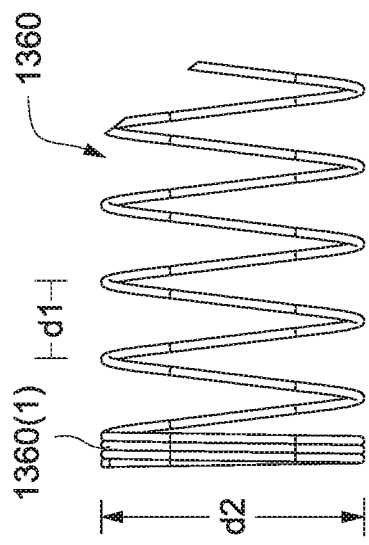
Figures 2, 50:
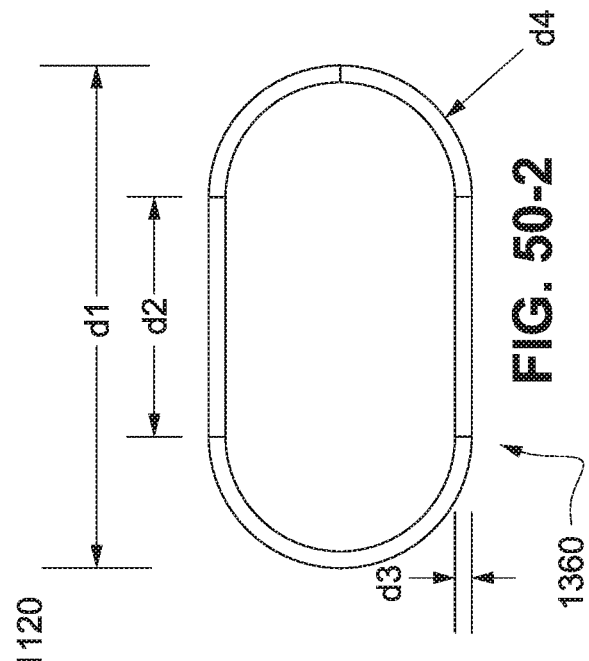
Figure 49:
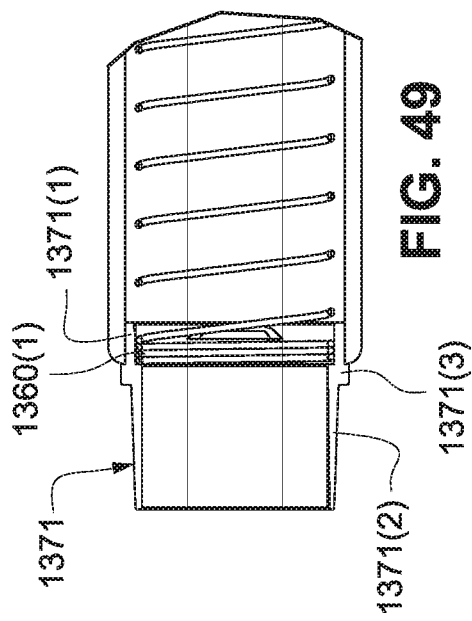
FIG. 49 is a cross-sectional view taken along the line 49-49 of the conduit in FIG. 46.

A wire substrate 1360 is inserted into the conduit to provide crush resistance and form. The wire substrate is in the form of a coil and can be made of stainless steel or any other suitable material. Each end of the wire substrate 1360 has a plurality of closed coils forming an end portion 1360(1) of the wire substrate, as shown in FIGS. 49 and 50-1. In this example, the end portion 1360(1) includes 3 closed coils.

A first cuff 1371 is attached to a first end of the wire substrate and a second cuff 1371 is attached to a second end of the wire substrate. The first cuff 1371 has a neck portion 1371(1) at a first end which engages one end portion 1360(1) of the wire substrate for securing the first cuff thereto. A connecting portion 1371(2) is provided at a second end of the first cuff 1371 and has a narrowing profile for connecting to a patient interface and/or a manifold. A flange 1371(3) separates the neck 1371(1) and the connecting portion 1371(2).

A second cuff 1372 has a neck portion 1372(1) at a first end which engages the other end portion 1360(1) of the wire substrate for securing the second cuff thereto. A connecting portion 1372(2) is provided at a second end of the second cuff 1372 for connecting to a patient interface and/or a manifold. A retaining wall 1372(3) and a clip member 1372(4) are disposed on an interior portion of the second cuff. The wire substrate 1360 is secured to the second cuff 1372 by clamping a portion of the wire substrate between the retaining wall 1372(3) and the clip member 1372(4). The first cuff 1371 may also have a retaining wall and clip member. Further, the cuffs 1371,1372 may be made of plastic or any other suitable material.

Referring to FIGS. 45, 47 and 48, in an example, d1 may be about 585-880 mm, e.g., 733.20 mm, d2 may be about 550-850 mm, e.g., 700 mm, d3 may be about 0.9-1.6 mm, e.g., 1.25 mm, d4 may be about 20-40 mm, e.g., 30.40 mm, d5 may be about 1.6-2.4 mm, e.g., 2 mm, and d6 may be about 12-20 mm, e.g., 16 mm. Additionally, the thickness of the neck 1371(1) may be about 0.9-1.6 mm, e.g., 1.25 mm.

In an example, as shown in FIG. 50-1, d1 may be about 5-9 mm, e.g., 7 mm, and d2 may be about 9.5-15.5 mm, e.g., 12.5 mm. Further, in an example, the length of the wire substrate 1360 may be similar to the distance d2 in FIG. 45.

Referring to FIG. 50-2, in an example, d1 may be about 20-28 mm, e.g., 23.9 mm, d2 may be about 9-13.8 mm, e.g., 11.4 mm, d3 may be about 0.5-1.1 mm, e.g., 0.8 mm, and the radius of curvature at d4 may be about 3.45-7.45 mm, e.g., 5.45 mm.

The conduit 1320 is air impermeable and form holding in use.

6. Non-Woven Tube

Figure 51:
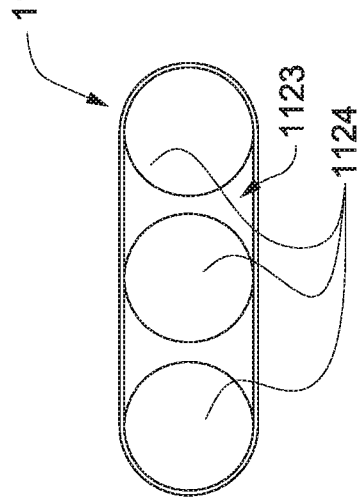
FIG. 51 is a cross-sectional view of an air delivery conduit according to an example of the disclosed technology.
Figure 52:
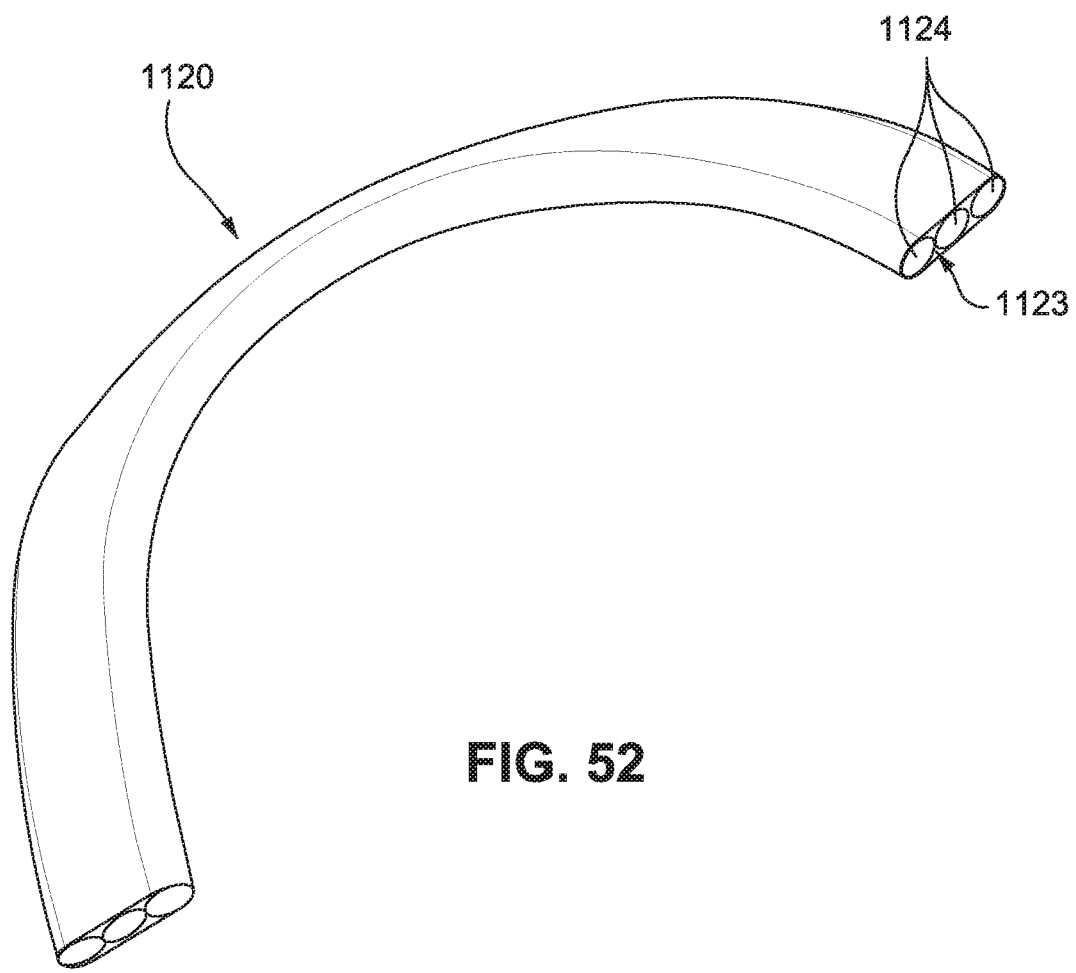
FIG. 52 is a perspective view of the conduit of FIG. 51.

FIGS. 51 and 52 show an air delivery conduit 1120 according to another example of the disclosed technology. In this example, the conduit is constructed of non-woven fibers (e.g., lightweight hydroentangled (spunlaced) fabrics) and includes an internal cavity 1123 filled with one or more particles (e.g., gels, waxes, cosmetics, detergents, and/or solid particles) to provide crush resistance and form. As illustrated, the particles may define one or more passages or lumens 1124 through the conduit. In an example, the exterior surface of the conduit may be coated.

7. Spacer Fabric

FIGS. 53-1 to 53-3 and 54 show an air delivery conduit 1220 according to another example of the disclosed technology. In this example, the air delivery conduit 1220 includes a tube 1225 constructed of spacer fabrics and textile cover portions 1231, 1232 (e.g., laminated fabric) that substantially enclose the tube. Laminated fabric in cohesion with spacer fabrics provides a crush resistant textile conduit. Such conduit is crush resistant, air impermeable, form holding, and includes possible in-built filtering qualities.

First and second textile cover portions 1231, 1232 cooperate to form a cover for the tube 1225, i.e., first textile cover portion provides a cover for a portion of the tube circumference and the second textile cover portion provides a cover for the remaining portion of the tube circumference. The textile cover portions 1231, 1232 may be constructed of a laminated fabric (e.g., an inner layer of a film laminate 1250 (e.g., polyurethane or medical grade film) and an outer layer of a textile or fabric 1255 (e.g., synthetic or specified fabric)), each of which may be thermoformed to create its shape and then the textile cover portions may be seam welded to couple the textile cover portions.

The tube 1225 is constructed of spacer fabrics including one or more outer layers 1225(1) (e.g., first and second layers) that cooperate to form the wall of the tube and an inner layer 1225(2) (e.g., third layer) supported within the internal passage provided by the one or more outer layers. The tube includes a relatively flat or non-cylindrical cross-section with the inner layer providing an anti-crush or occlusion resistant structure. The inner layer may define one or more passages or lumens through the tube.

Figures 1, 53:
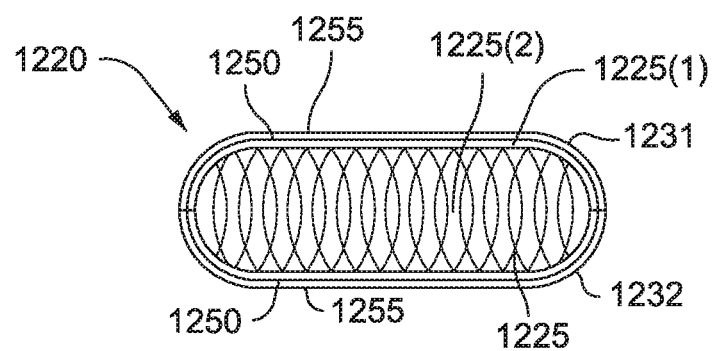
Figures 2, 53:
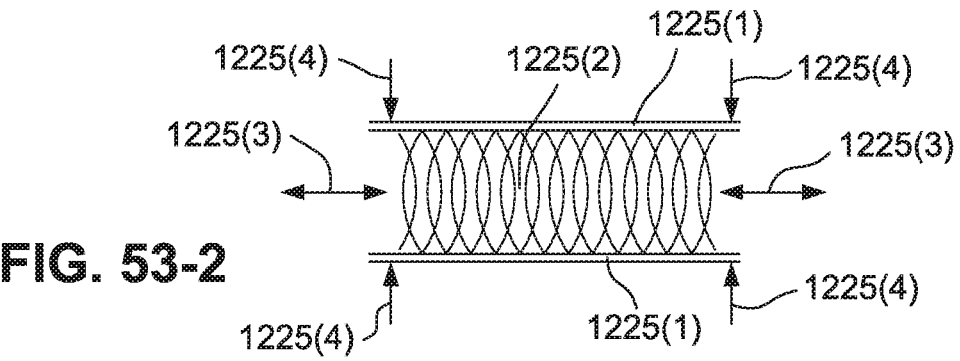
Figures 3, 53:
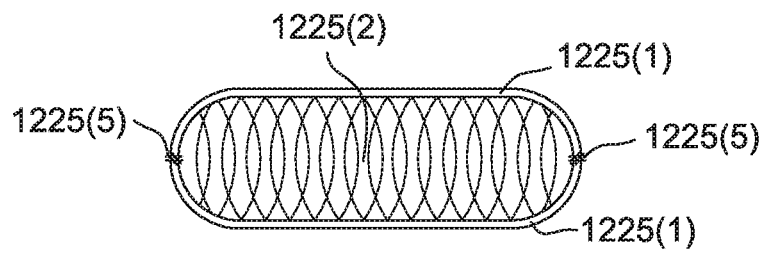
Figure 54:
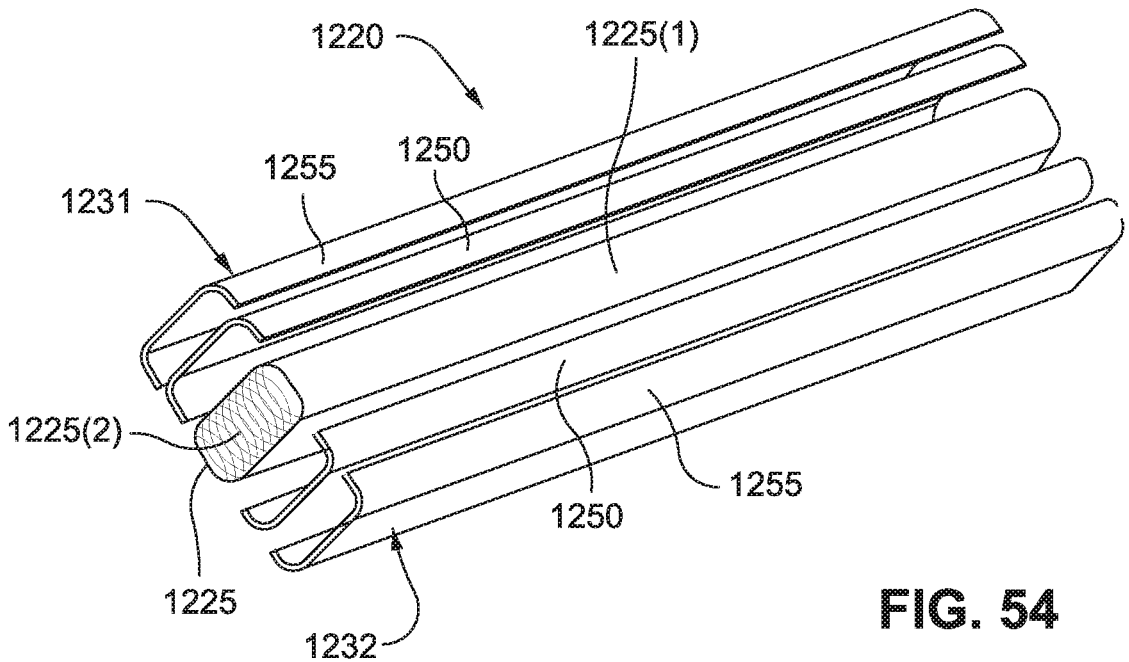
FIG. 54 is an exploded view of the conduit of FIG. 53.

The tube 1225 may be made with upper and lower layers 1225(1) and an inner layer 1225(2) as shown in FIGS. 53-2 and 53-3. Preferably, the inner layer 1225(2) my have a width that is less than the upper and lower layers 1225(1) such that the upper and lower layers 1225(1) overhang the inner layer 1225(2) as shown by the arrows 1225(3). The upper and lower layers 1225(1) may then be squeezed together as shown by the arrows 1225(4) and stitched together at 1225(5) to form a conduit or tube such that the inner layer 1225(2) is enclosed within the upper and lower layers 1225(1). It should be appreciated that the upper and lower layers may be connected by means other than stitching 1225(5).

The inner layer 1225(2), also known as the pile, may have a density. The density may be varied to alter the stiffness and/or flow impedance of the tube. For example, the density may be high to ensure the tube is stiff enough to resist crush and/or kink forces. The density may be low to ensure the impedance of the air running through the tube is low enough to prevent significant pressure losses.

The structure of the inner layer or pile 1225(2) may be systematic or methodical, such as an even spread of threads. Alternatively, the structure of the inner layer or pile 1225(2) may be random or disorderly.

The tube 1225 may be thermoformed in order to impart a shape on the tube. For example, the tube 1225 may be constructed of or include in its construction a heat deformable material such as a polymer (for example nylon, polypropylene), such that when it is heated, it may be altered in shape and maintain that shape when cooled.

FIGS. 55 to 71 illustrate alternative configurations of a fabric tube. The fabric tube may be constructed of a spacer fabric. Alternatively, the fabric may be a woven or non-woven fabric tube adapted to receive a tube i.e. the fabric may be a sock or a sleeve.

Figure 55:
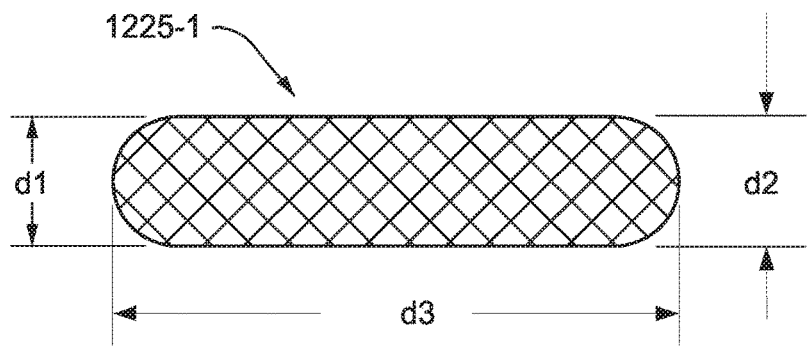
FIG. 55 shows a spacer fabric for the conduit of FIG. 53 according to an alternative example of the disclosed technology.

In FIG. 55, the inner layer of the spacer fabric 1225-1 provides a grid-like internal passage. In an example, as shown in FIG. 45, d1 may be about 8-12 mm, e.g., 9.5 mm, d2 may be about 8-12 mm, e.g., 10 mm, and d3 may be about 30-50 mm, e.g., 40.5 mm.

In FIGS. 56-61, the inner layer of the spacer fabric 1225-2 has a pile density that varies along the width of the spacer fabric such that channels 1225(6) are provided in less dense areas. In the example shown, four channels are provided. However, any suitable number of channels 1225(6) can be provided in order to optimize airflow and/or structural integrity. The spacer fabric may be composed of nylon and/or polyester, or any other suitable materials.

Figure 56:
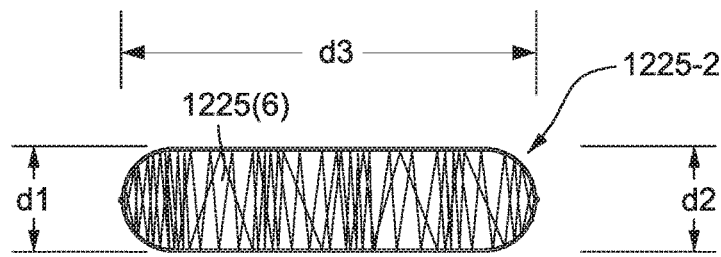
FIG. 56 is a cross-sectional view of a spacer fabric in accordance with an alternative example of the disclosed technology.
Figure 57:
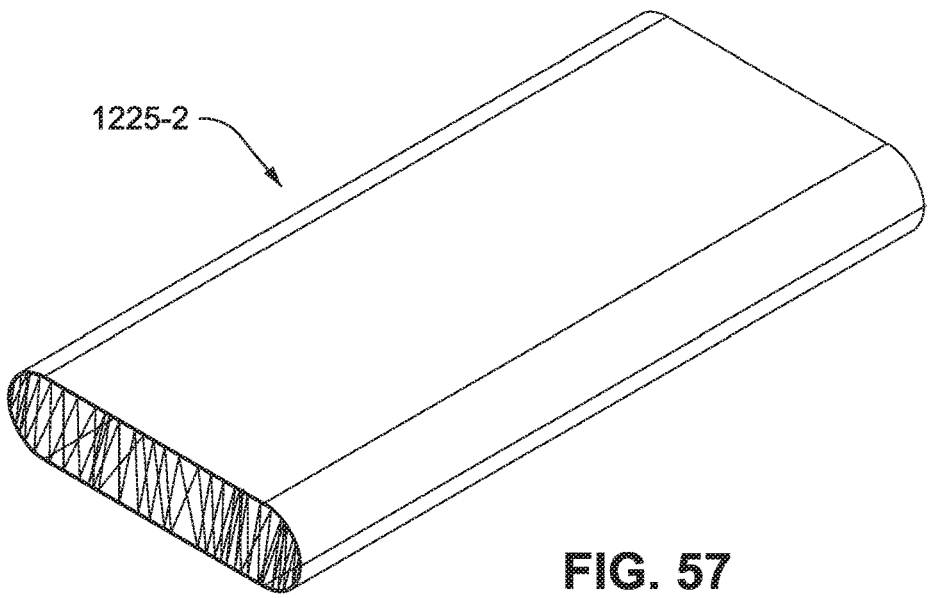
FIG. 57 is a perspective view of the spacer fabric of FIG. 56.
Figure 58:
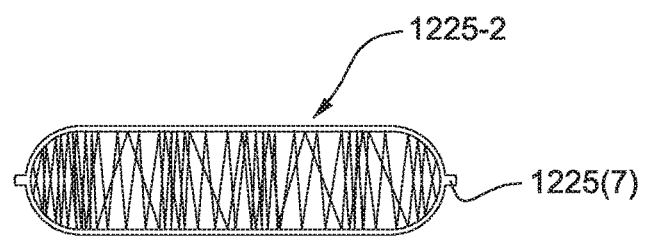
FIG. 58 is a cross-sectional view of the spacer fabric of FIG. 57 according to an alternative example of the disclosed technology.
Figure 59:
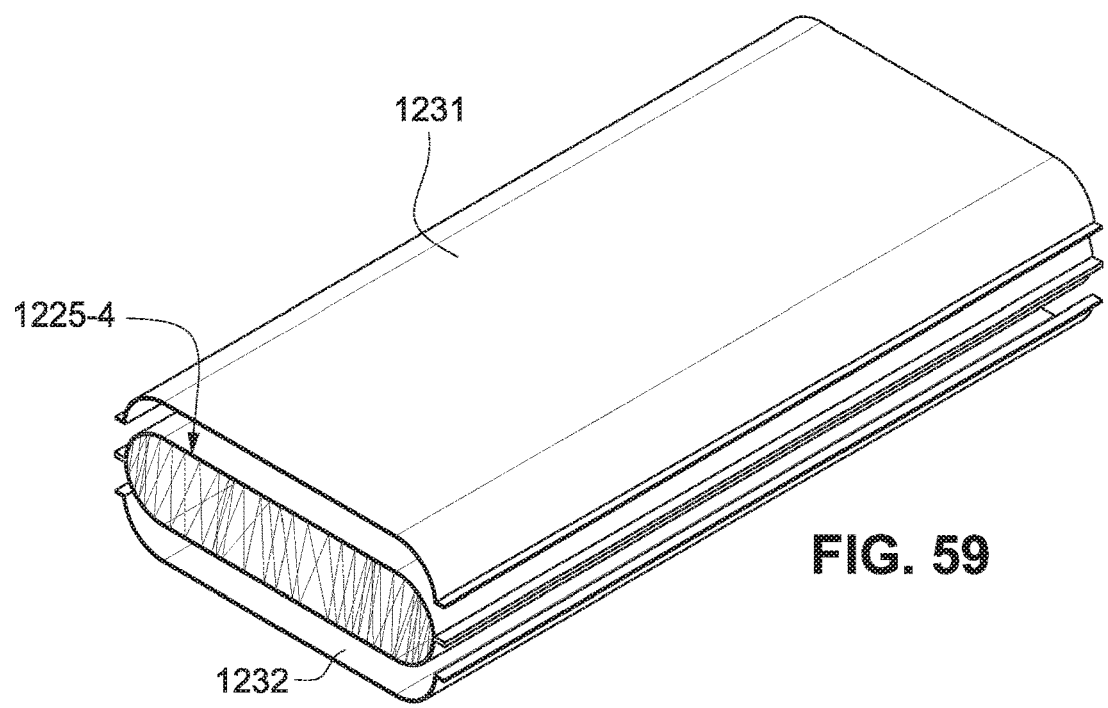
FIG. 59 is an exploded view of an air delivery conduit according to an example of the disclosed technology.
Figure 60:
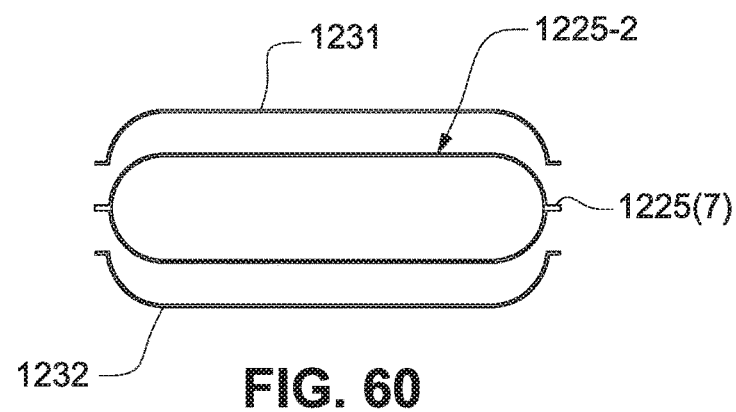
FIG. 60 is an exploded cross-sectional view of the conduit of FIG. 59.
Figure 61:
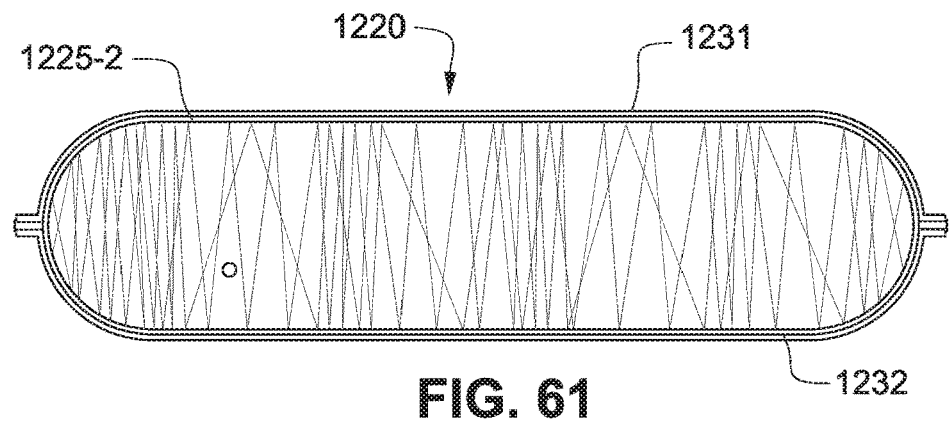
FIG. 61 is a cross-sectional view of the conduit of FIG. 59.

The spacer fabric can be coated with a layer of silicone to make the spacer fabric airtight, as shown in FIGS. 56 and 57. Alternatively, as shown in FIG. 58-61, the spacer fabric 1225-2 could have flanges 1225(7) on opposite sides to provide weld points for fabric laminate sheets 1231,1232. In an example, as shown in FIG. 56, d1 may be about 8-12 mm, e.g., 9.5 mm, d2 may be about 8-12 mm, e.g., 10 mm, and d3 may be about 30-50 mm, e.g., 40 mm. Further, in an example, the length of the spacer fabric 1225-2 may be about 150-2500 mm, e.g., 300 mm, 670 mm, or 2000 mm.

Figure 62:
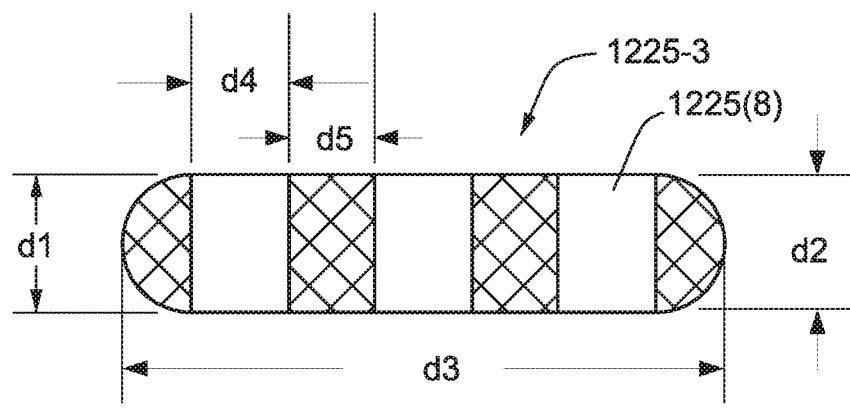
FIG. 62 is a cross-sectional view of a spacer fabric in accordance with an alternative example of the disclosed technology.

In FIG. 62, the inner layer of the spacer fabric 1225-3 includes grid-like internal walls that define three generally rectangular lumens 1225(8) though the tube. However, the inner layer may define any suitable number of lumens with other suitable shapes, e.g., one, two, four or more lumens. In an example, as shown in FIG. 62, d1 may be about 8-12 mm, e.g., 9.5 mm, d2 may be about 8-12 mm, e.g., 10 mm, and d3 may be about 30-50 mm, e.g., 42 mm. The width d4 of each lumen may be about 5-10 mm, e.g., 6.7 mm, and the width d5 of an internal wall defining the lumens may be about 5-10 mm, e.g., 6 mm, as shown in FIG. 62. In alternative examples, one or more of the lumens can have widths and/or heights that are different from those of the other lumens.

Figure 63:
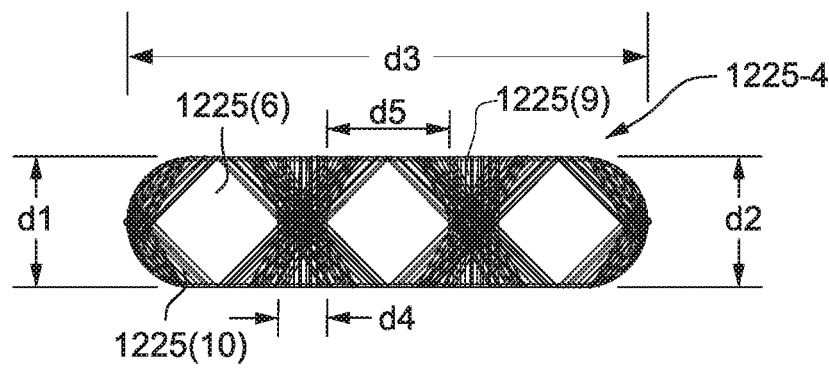
FIG. 63 is a cross-sectional view of a spacer fabric in accordance with an alternative example of the disclosed technology.
Figure 64:
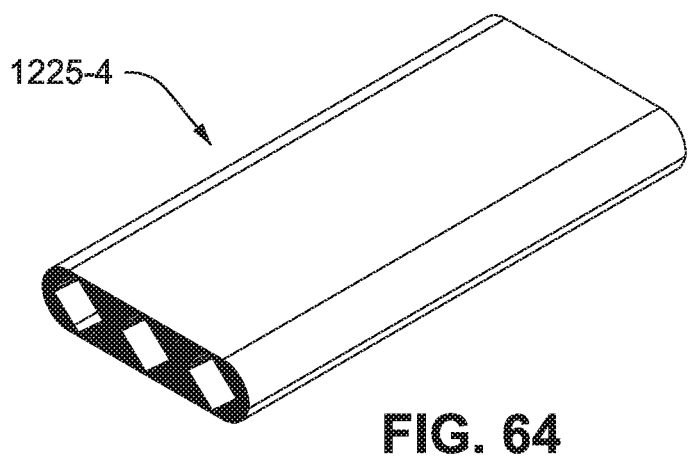
FIG. 64 is a perspective view of the spacer fabric of FIG. 63.
Figure 65:
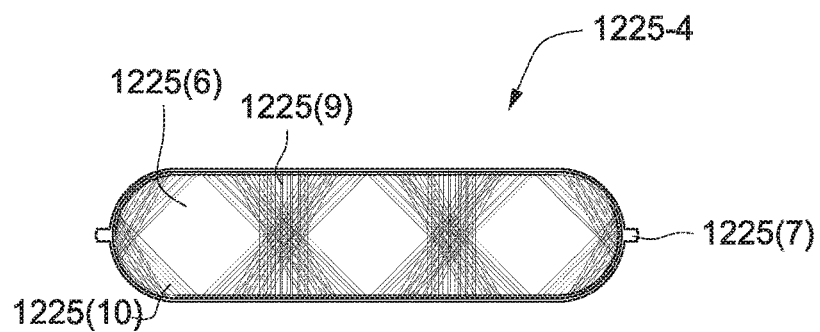
FIG. 65 is a cross-sectional view of the spacer fabric of FIG. 63 according to an alternative example of the disclosed technology.
Figure 66:
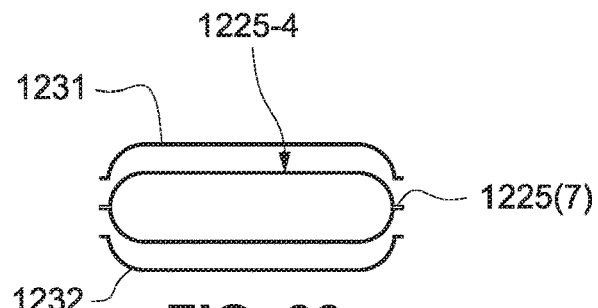
FIG. 66 is an exploded cross-sectional view of an air delivery conduit according to an example of the disclosed technology.
Figure 67:
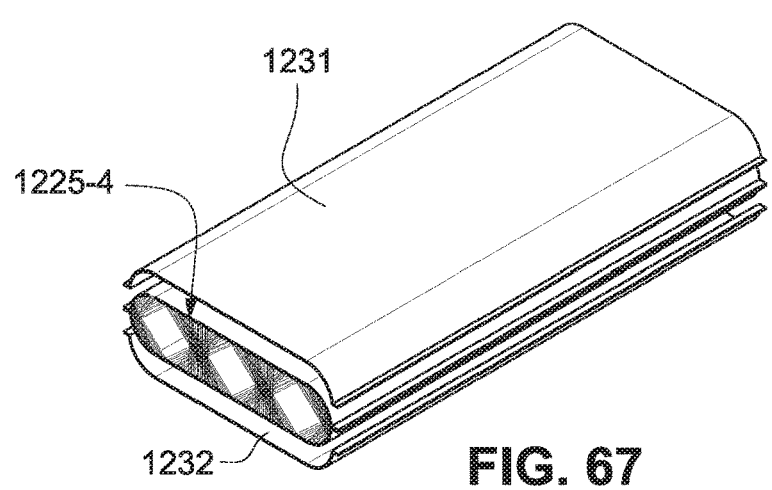
FIG. 67 is an exploded perspective view of the conduit of FIG. 66.
Figure 68:
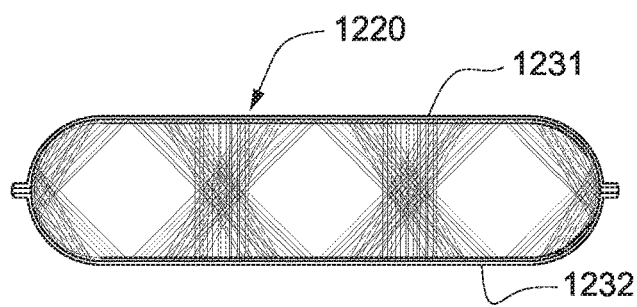
FIG. 68 is a cross-sectional view of the conduit of FIG. 66.

In FIGS. 63-68, the spacer fabric 1225-4 has a plurality of channels 1225(6) separated by occlusion resistant columns 1225(9) and shear resistant diagonals 1225(10) of spacer pile. The spacer fabric may be composed of nylon and/or polyester, or any other suitable materials. One skilled in the art would recognize that any suitable number of channels 1225(6), columns 1225(9) and diagonals 1225(10) may be provided in order to optimize airflow and/or structural integrity. The spacer fabric can be coated with a layer of silicone to make the spacer fabric airtight, as shown in FIGS. 63 and 64. Alternatively, as shown in FIGS. 65-68, the spacer fabric 1225-4 could have flanges 1225(7) on opposite sides to provide weld points for fabric laminate sheets 1231,1232. In an example, as shown in FIG. 63, d1 may be about 8-12 mm, e.g., 9.5 mm, d2 may be about 8-12 mm, e.g., 10 mm, d3 may be about 30-50 mm, e.g., 40 mm, d4 may be about 2.7-5 mm, e.g., 3.85 mm, and d5 may be 8-12 mm, e.g., 9.5 mm. Further, in an example, the length of the spacer fabric 1225-4 may be about 150-2500 mm, e.g., 300 mm, 670 mm, or 2000 mm.

Figure 69:
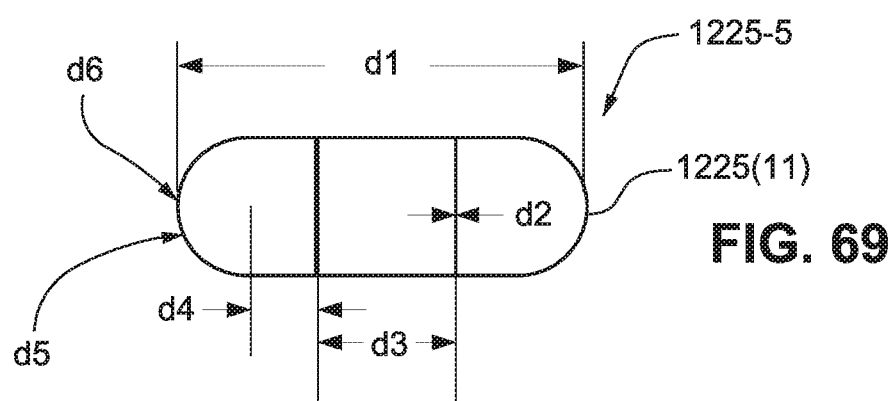
FIGS. 69-71 show spacer fabrics for the conduit of FIG. 53 according to alternative examples of the disclosed technology.

In FIG. 69, the inner layer of the spacer fabric 1225-5 includes relatively thin internal walls that define three lumens 1225(11) through the tube. However, the inner layer may define any suitable number of lumens with other suitable shapes. In an example, as shown in FIG. 69, d1 may be about 20-40 mm, e.g., 29.5 mm, d2 may be about 0.1-0.5 mm, e.g., 0.25 mm, d3 may be about 5-10 mm, e.g., 9.5 mm, d4 may be about 2-10 mm, e.g., 4.75 mm, the radius of curvature at d5 may be about 3-7 mm, e.g., 5 mm, and the radius of curvature at d6 may be about 3-7 mm, e.g., 4.75 mm.

Figure 70:
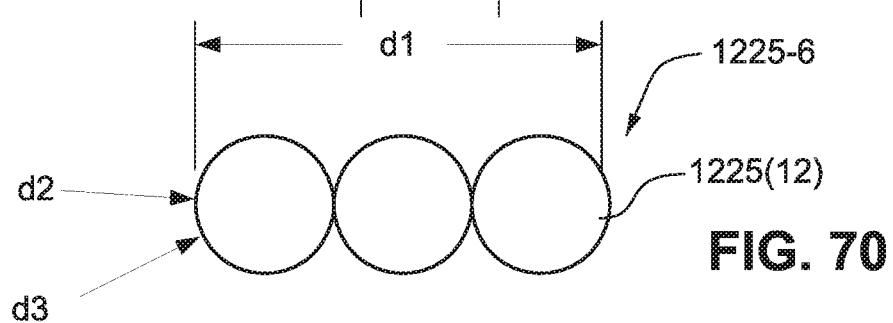

In FIG. 70, the spacer fabric 1225-6 is in the form of three adjoined cylindrical lumens 1225(12). However, the spacer fabric may define any suitable number of lumens with other suitable shapes. In an example, as shown in FIG. 70, d1 may be about 20-40 mm, e.g., 29.5 mm, the radius of curvature at d2 may be about 3-7 mm, e.g., 5 mm, and the radius of curvature at d3 may be about 3-7 mm, e.g., 4.75 mm.

Figure 71:
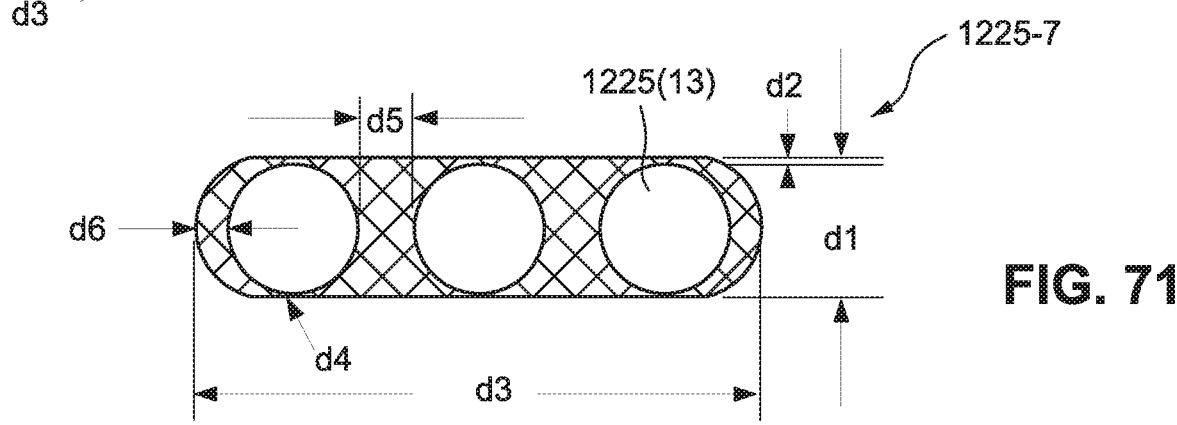

In FIG. 71, the inner layer of the spacer fabric 1225-7 includes grid-like internal walls that define three generally cylindrical lumens 1225(13) through the tube. However, the inner layer may define any suitable number of lumens with other suitable shapes. In an example, as shown in FIG. 71, d1 may be about 8-12 mm, e.g., 10 mm, d2 may be about 0.1-0.5 mm, e.g., 0.25 mm, d3 may be about 30-50 mm, e.g., 40.5 mm, the radius of curvature at d4 may be about 3-7 mm, e.g., 4.75 mm, d5 may be about 2-6 mm, e.g., 3.8 mm, and d6 may be about 1-5 mm, e.g., 2.2 mm.

8. High Density Fabric Cover

Figure 72:
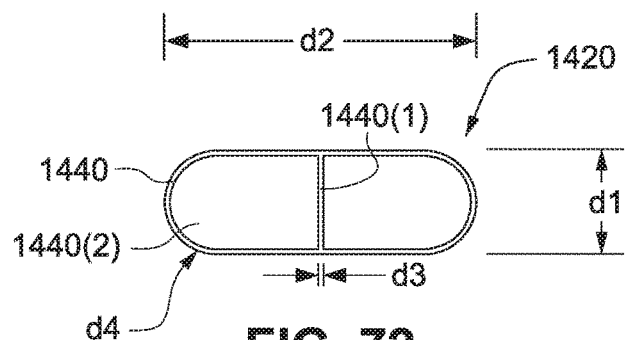
FIGS. 72 and 73 are cross-sectional views of air delivery conduits according to examples of the disclosed technology.
Figure 73:
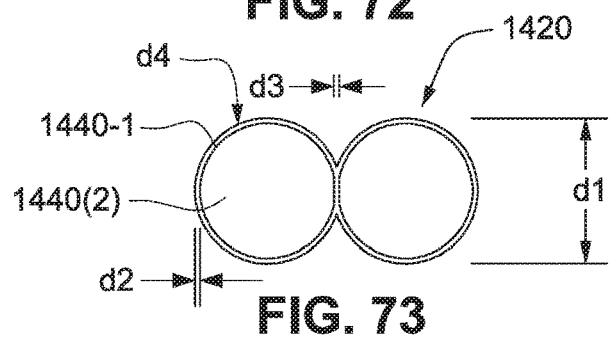
Figure 74:
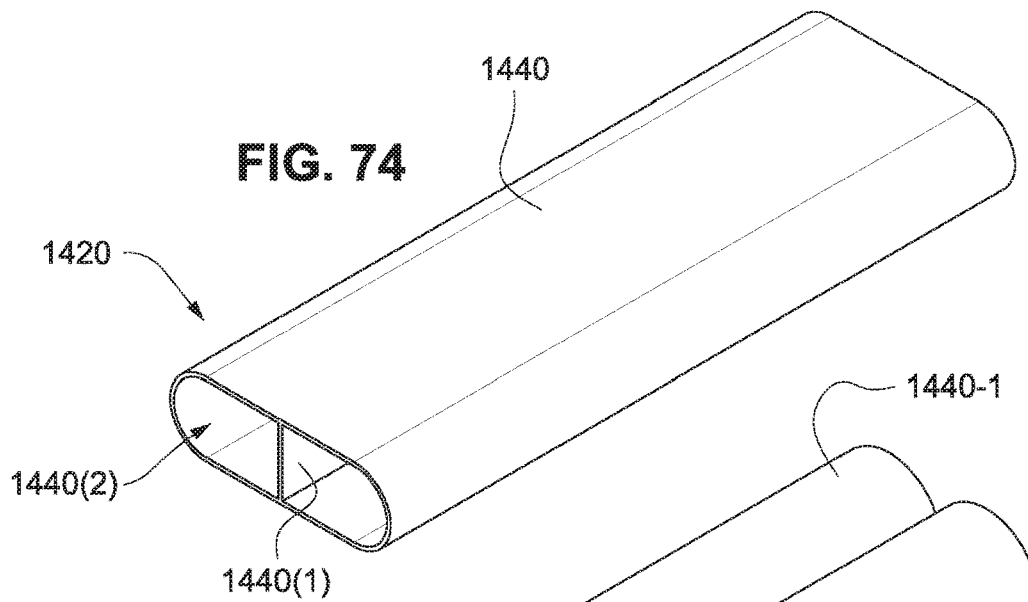
FIG. 74 is a perspective view of the air delivery conduit of FIG. 72.

FIGS. 72-76 show an air delivery conduit 1420 according to another example of the disclosed technology. In one example, the air delivery conduit 1420 includes a fabric cover 1440 constructed of a warp-knitted fabric having a high fabric density. The fabric cover may be composed of nylon and/or polyester, or any other suitable materials. The fabric cover 1440, as shown in FIGS. 72 and 74, includes an internal wall 1440(1) which provides separate channels 1440(2) for conveying pressurized gas. In the illustrated example, a single internal wall 1440(1) is provided thereby creating two channels 1440(2). However, any suitable number of channels can be provided by employing additional internal walls 1440(1). In an example, d1 may be about 8-12 mm, e.g., 9.5 mm, d2 may be about 20-40 mm, e.g., 30 mm, d3 may be about 0.3-0.7 mm, e.g., 0.5 mm, and the radius of curvature at d4 may be about 3-7 mm, e.g., 5 mm. Further, in an example, the length of the fabric cover 1440 may be about 150-2500 mm, e.g., 300 mm, 670 mm, or 2000 mm.

Figure 75:
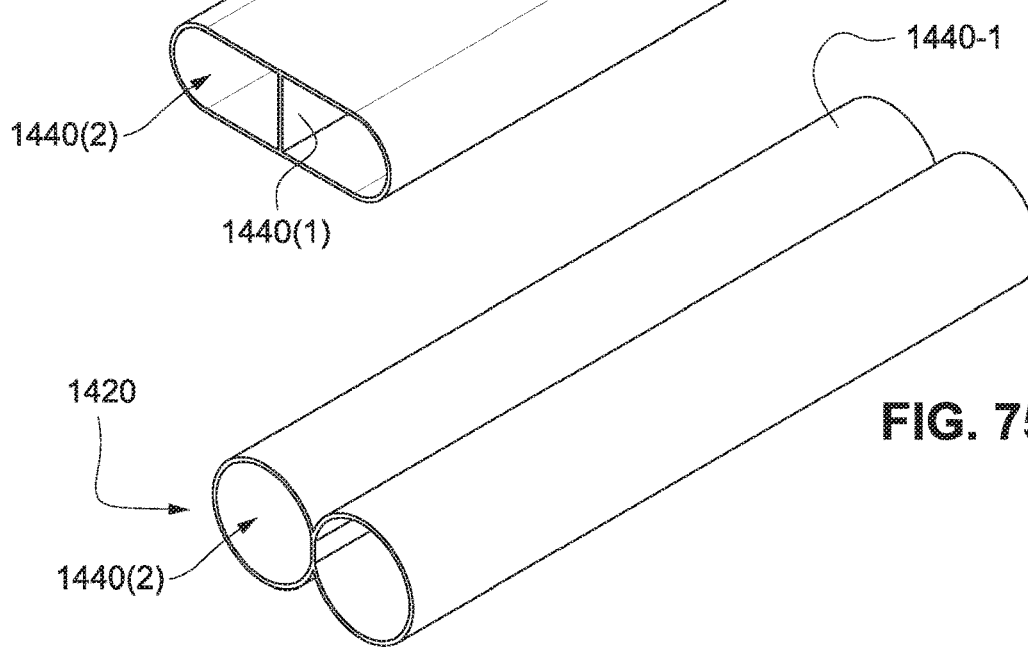
FIG. 75 is a perspective view of the air delivery conduit of FIG. 73.
Figure 76:
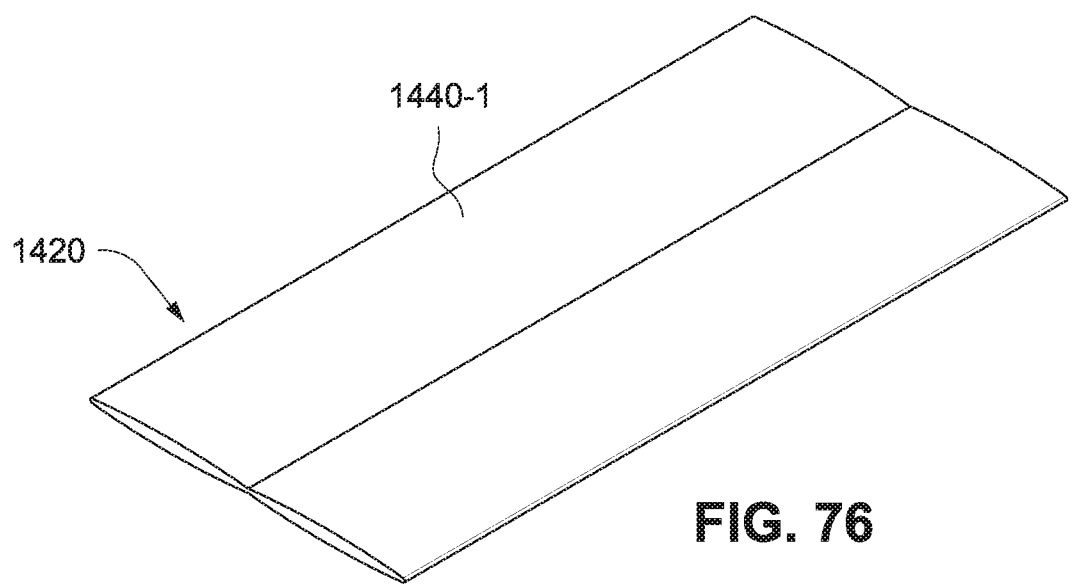
FIG. 76 is a perspective view of the air delivery conduit of FIG. 73, shown in a flat configuration.

In another example, a fabric cover 1440-1, as shown in FIGS. 73 and 75, is formed by knitting two adjoining cylindrical shapes, thereby forming channels 1440(2). One skilled in the art would recognized that any suitable number of cylindrical shapes could be formed, and further that the channels 1440(2) could be formed by other shapes. Further, the cross-sectional shapes and/or dimensions of the channels may vary from channel to channel. As shown in FIG. 76, the fabric cover 1440-1 can assume a substantially flat configuration when either no air or a small amount of air is being conveyed through the fabric cover. The ability of the fabric cover 1440-1 to change form is advantageous for storing and transporting the fabric cover. In an example, d1 may be about 10-18 mm, e.g., 14 mm, d2 may be about 0.3-0.7 mm, e.g., 0.5 mm, d3 may be about 0.3-0.7 mm, e.g., 0.5 mm, and the radius of curvature at d4 may be about 4.5-8.5 mm, e.g., 6.5 mm. Further, in an example, the length of the fabric cover 1440-1 may be about 150-2500 mm, e.g., 300 mm, 670 mm, or 2000 mm.

9. Integrated One-Piece Composite

FIGS. 77-1 to 77-2 illustrate a process of forming an air delivery conduit according to another example of the disclosed technology. In the example shown in FIG. 77-1, a textile substrate may be provided with a support structure 1540 to form an integrated one-piece composite self-supporting textile conduit 1520. The textile substrate is preferably a fabric that is air-resistant or completely air-tight (e.g., may include film laminate or air-tight layer). The support structure 1540 may comprise a rib structure including one or more rib formations.

Several methods may be used to form the support structure 1540 on the textile substrate 1530 and to form the textile substrate into the air delivery conduit 1520. For example, a rigid or semi-rigid rib structure may be overmolded onto the textile substrate 1530, and the textile substrate may be formed into a conduit during or after the overmolding process. The support structure 1540 may be formed of a polymer.

In another example, the textile substrate 1530 may be inserted into a relatively flat tool and a support structure may be molded in a pattern on top of the substrate to provide a level of controlled flexibility/rigidity. The support structure may include a series of parallel ribs, a half-helix, etc. Even with the addition of the overmolded support structure 1540, the textile substrate remains a substantially flat two-dimensional structure which can be rolled or folded into a tubular structure. Opposing edges may then be connected to form a side seam, thus forming the conduit 1520.

Referring particularly to FIG. 77-1, the textile substrate is combined with the support structure 1540 which includes a plurality of parallel ribs. The support structure 1540 comprises a stiffer or slightly thicker material than the textile substrate. The ribs are formed to extend substantially transversely to a common axis, which may or may not be associated with a longitudinal axis of the substrate (or portion of the substrate). In addition to overmolding, the support structure 1540 may also be formed by attaching (e.g., by adhering, bonding, gluing, or stitching) thin slices of a material (e.g., a sheet metal or a polymer rigidizer) to the surface of the fabric. Such material may also be sandwiched between an upper and a lower layer of the textile substrate 1530.

The textile substrate 1530 including integrated rib structure is then rolled or folded upon itself, cut and seamed in order to form a tubular conduit structure having a seam 1565, as shown in FIG. 77-1. As a result of rolling/folding, the ribs form a series of parallel rings spaced along the length of the conduit 1520, as shown in FIGS. 77-1 and 77-1A.

Referring to FIGS. 77-2 and 77-2A, a process of forming an air delivery conduit 1520-1 similar to that shown in FIG. 77-1 is illustrated. In contrast to the conduit 1520, the conduit 1520-1 includes a support structure 1540-1 (e.g., ribs) that extends at an oblique angle (e.g., less than 90°, e.g., 30-90°, e.g., 40-90°, or about 45-90°) with regards to the common axis that coincides with the longitudinal axis of the intended conduit.

In another example of an air delivery conduit 1520-2, if the ribs are parallel to each other and the angle and the spacing of the ribs are suitably chosen, upon folding the substrate, the ribs of a support structure 1540-2 form a helix-type construction due to the particular angle of the ribs in relation to the direction of the folding or rolling, i.e., an end of a first rib may be aligned with an end of a second rib, as shown in FIG. 77-2B. The resulting structure may be a single, double or even triple helix, depending on whether a rib aligns with the end of an adjacent on nonadjacent rib. Arrangements, in which the ribs may not be parallel to each other, or may not necessarily be aligned with other ribs, are also possible.

Figures 1, 78:
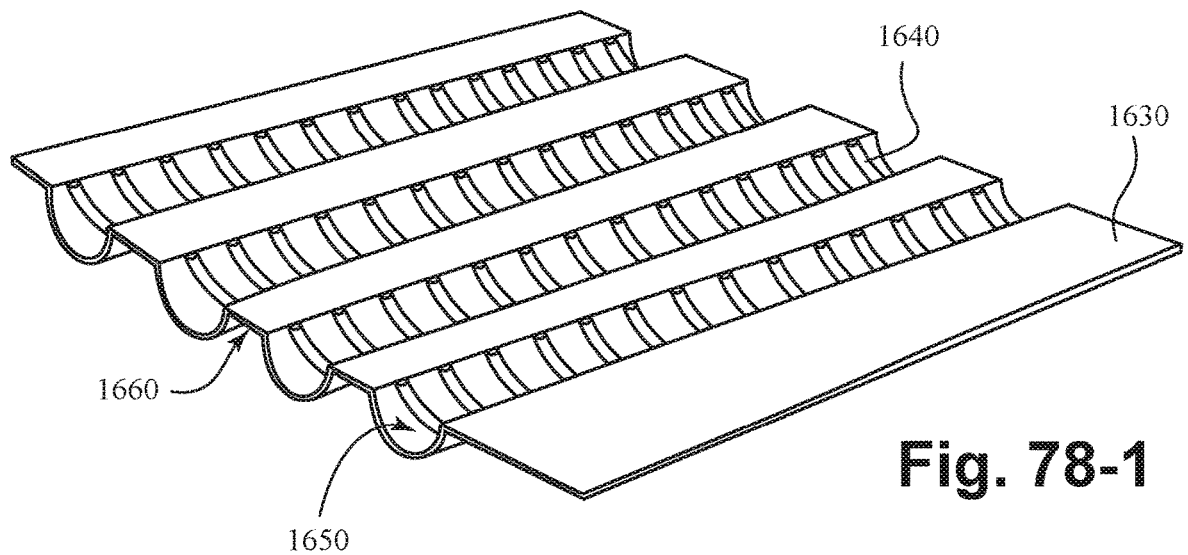
Figures 2, 78:
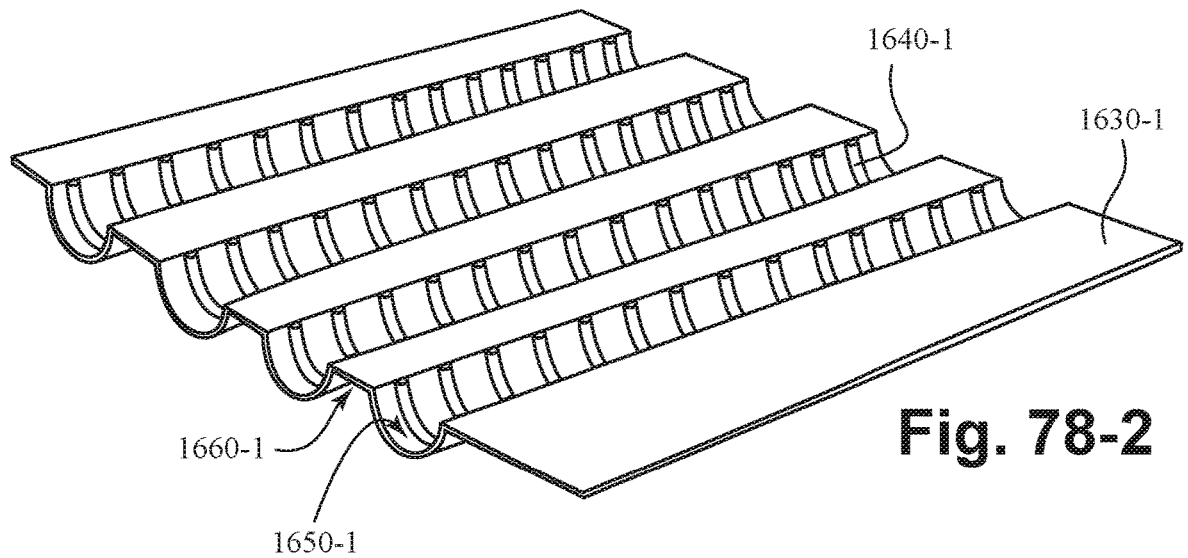

Referring to FIGS. 78-1 and 78-2, a substantially flat textile substrate may be inserted into a tool that has a curved or a three dimensional shape to perform the overmolding process. During the overmolding process, the textile substrate may also be thermoformed or heat/pressure-affected such that the textile substrate emerges from the tool with an overmolded support structure and the three dimensional shape of the overmolding tool. A specific desired three dimensional shape may be beneficial for the further processing of the substrate (e.g., in forming the final conduit structure).

Referring particularly to FIG. 78-1, a thermoformed and overmolded textile substrate 1630 includes a series of half-pipe or half-tube shapes (e.g., series of concave formations 1650 with interspersed planar sections 1660). The support structure 1640 forms a half-helix pattern on an interior of the concave formations 1650.

FIG. 78-2 shows a textile substrate 1630-1 similar to the textile substrate 1630 and including a support structure 1640-1, concave formations 1650-1 and planar sections 1660-1. In contrast to the textile substrate 1630, the support structure 1640-1 of the textile substrate 1630-1 forms a pattern of parallel raised ribs (lines) on the interior of the concave formations 1650-1.

Turning to FIG. 78-3, a process of rolling or folding the textile substrates 1630, 1630-1 so that two half-pipe shapes can be fused together into a closed continuous pipe-like structure is shown. An air delivery conduit 1620, 1620-1 may include two similar half-pipe portions resulting in two distinctive seams 1665, as shown in FIG. 78-4. The seams may be formed by ultrasonically welding overlapping flanges 1662, or a butt-weld configuration, sewing, seam taping, overlocking, heat-fusing, RF welding, gluing or other suitable methods.

In another example, instead of folding a single substrate onto itself, a plurality of conduits may be formed by aligning two separate substrates against each other such that each half-pipe portion of the first substrate is aligned against a respective half-pipe portion of the second substrate. The overlapping portions of the adjacently formed conduits may then be seamed as described above in reference to FIG. 78-3.

In another example, a closed continuous pipe may be formed with just one distinctive edge along its length by rolling one half-pipe shape onto itself and then attaching the long edges together. The folded textile substrate may be die-cut and heat-pressed to remove excess material and create a seam join 1765, as shown in FIG. 78-5. This single seem join 1765 of the conduit 1720 is more discreet and hidden, as opposed to being raised on the outer surface of the conduit in the manner of the seam 1665 in FIG. 78-4.

Figures 1, 79:
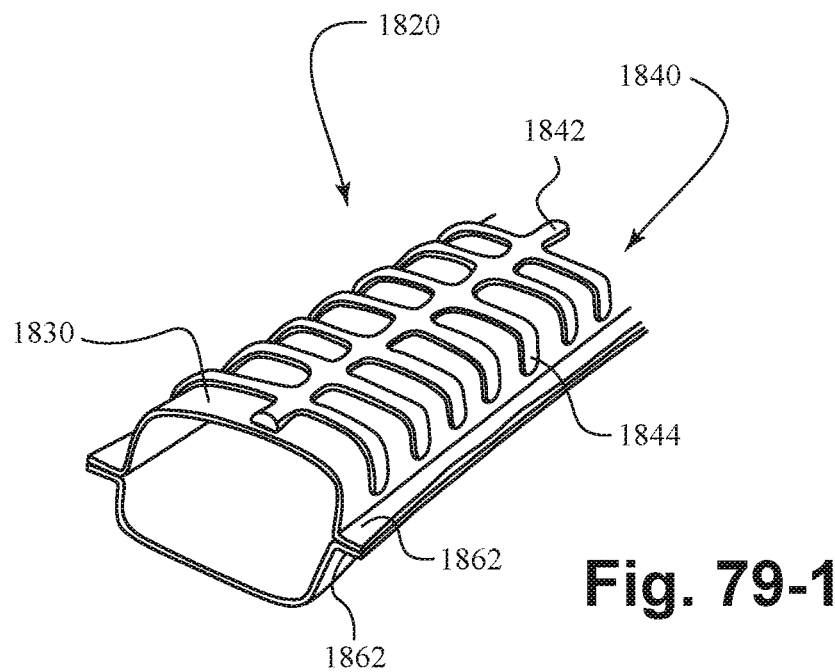
Figures 2, 79:
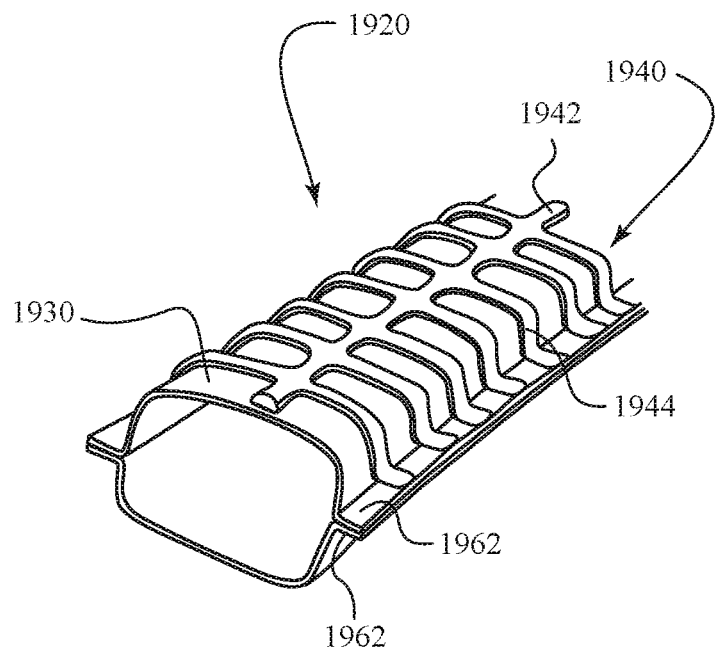

Turning to FIG. 79-1, an air delivery conduit 1820 including a textile 1830 formed into a tubular shape and a support structure 1840 adhered (e.g., by overmolding) to the textile is shown. The support structure 1840 provides structural integrity (e.g., support and resistance to deformation) and controlled flexibility to the textile 1830. The support structure may comprise a polymer overmolded onto the flexible substrate. The support structure includes a spine 1842 and a plurality of ribs 1844 extending from the spine 1842. The length of the ribs as well as the spacing between the ribs may be modified to obtain a desired level of rigidity, support, flexibility and/or resistance to deformation. As shown in FIG. 79-1, the support structure 1840 is situated on an exterior surface of the textile 1830.

Referring to FIG. 79-2, an air delivery conduit 1920 includes a textile 1930 and a support structure 1940. The support structure 1940 includes a spine 1942 and a plurality of ribs 1944. The conduit 1920 is similar to the conduit 1820 except that the ribs 1944 extend down to the flanges 1962 which form the side seam of the conduit 1920. This arrangement provides enhanced compression-resistance and control of the conduit shape.

In another example, the support structures 1840, 1940 could be formed on an internal surface of the textiles 1830, 1930.

Figures 1, 80:
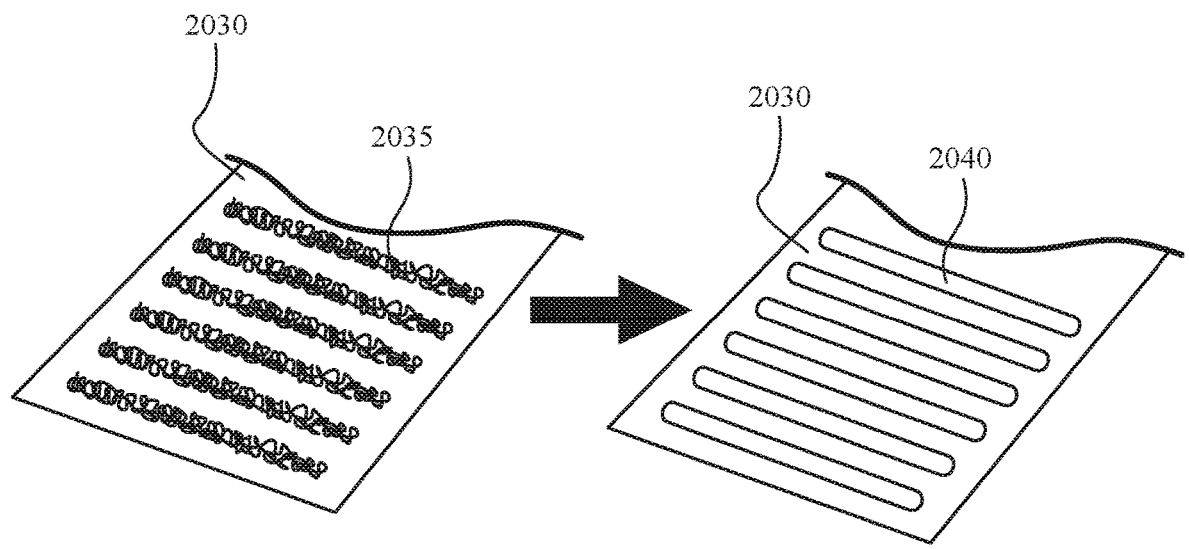
Figures 2, 80:
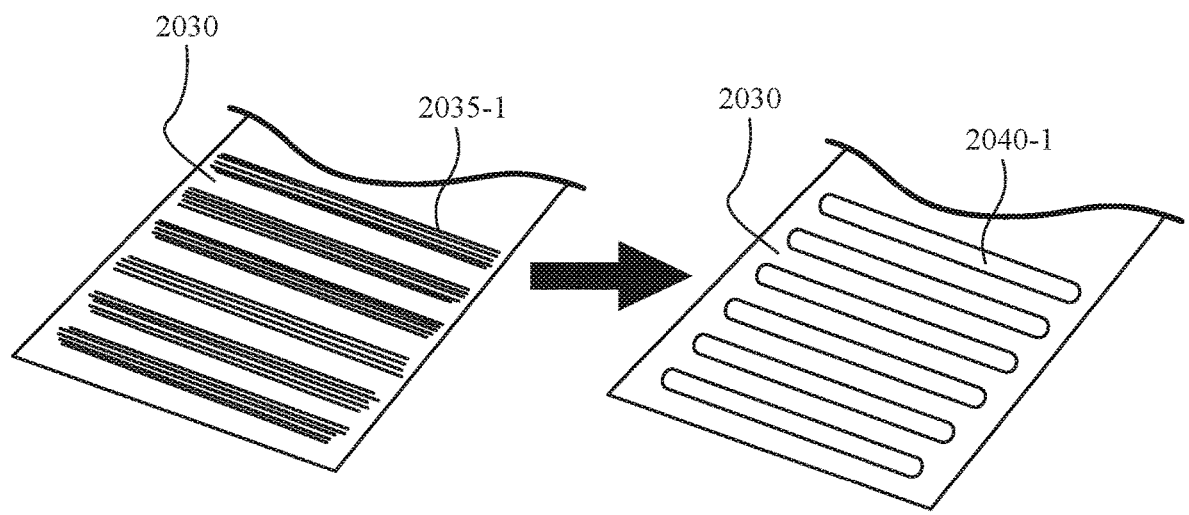
Figures 3, 80:
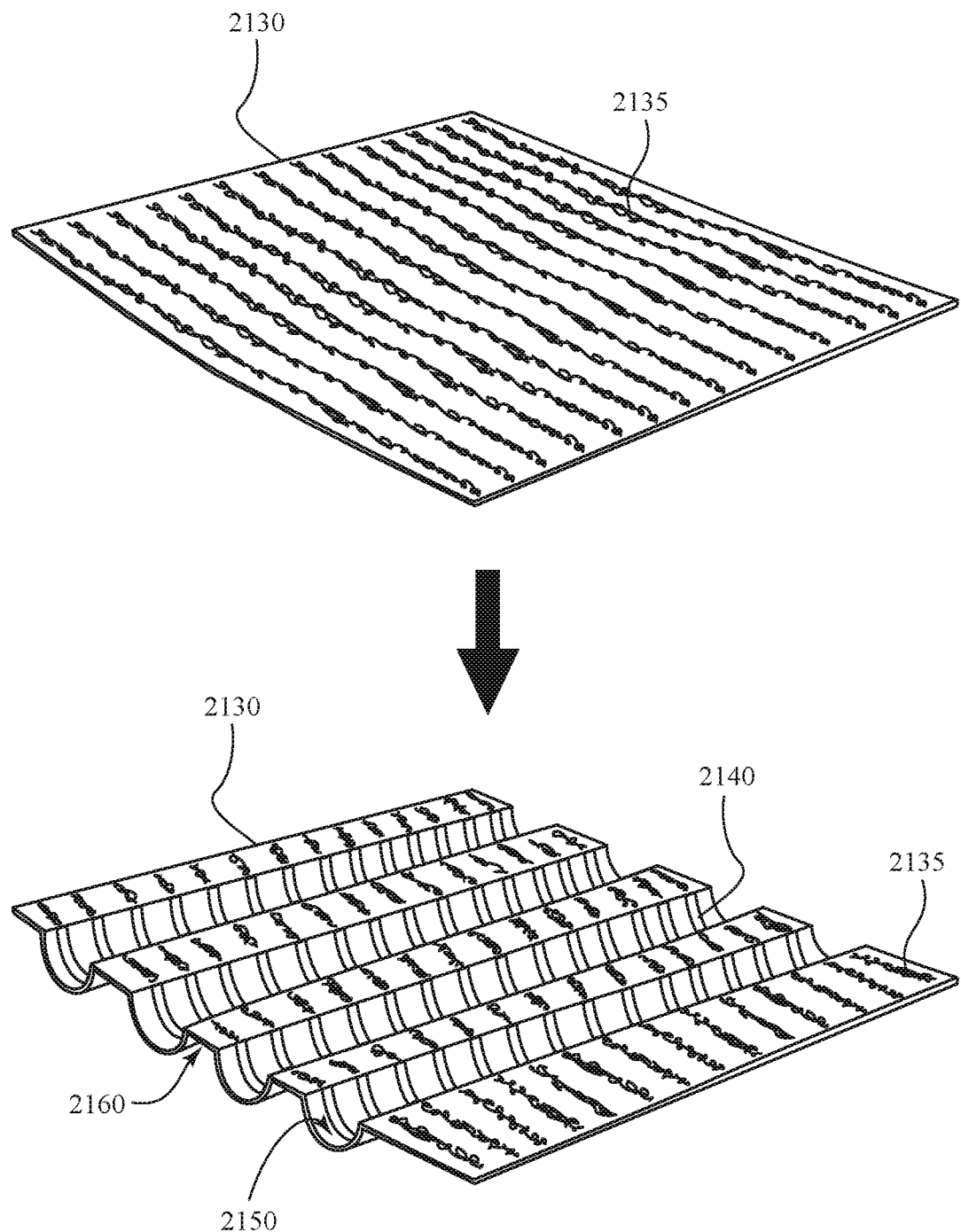

Referring to FIG. 80-1, a process of forming an air delivery conduit according to another example is shown. A base textile substrate 2030 having a first melting temperature may have support elements 2035 of a relatively lower melting temperature embedded therein to form a support structure 2040 by application of heat. For example, the melting temperature of nylon, which may form the base fabric, may be between 220° C. and 265° C., whilst the melting temperature of polypropylene, which may form the embedded element, may be between 160° C. and 165° C. Such embedded support structure 2040, when thermally processed, may provide rigidity, controlled flexibility and/or compression resistance for example. The textile substrate 2030 may comprise a flexible textile including primarily fibres/yarns or a sheet material of a certain melting temperature. The embedded support elements 2035 may include fibres/yarns of a lower melting temperature. The support elements 2035 may include polyester, polypropylene or others. The support elements 2035 may be woven, embroidered, weft-inserted, crocheted, braided, felted, fused or knitted into the textile substrate 2030 during or after the manufacturing process of the flat textile substrate fabric. The flexible textile substrate is preferably air-resistant or air-tight and may include a composite laminate or other textile structure.

The textile substrate 2030 (with the embedded support elements 2035) is then inserted into a heated tool or flat-plate press. The thermal processing causes the support elements 2035, which are of a lower melting temperature, to fuse together, and create a level of in-built rigidity within the textile substrate in the form of support structure 2040. The fused support elements 2035 are typically more rigid than the textile substrate 2030 and may be visible on one or both sides of the structure. Also, after the thermal processing, the fused elements may become integral to the overall structure.

This embedded textile substrate could then be rolled or folded and then seamed/joined along its long edges to form a compression-resistant flexible tube (in the manner shown in FIGS. 77-1 and 77-2).

In the arrangement shown in FIG. 80-2, each support element 2035-1 includes a number of fibres or yarns that are spaced closely together and extend substantially parallel to each other along an axis that is substantially transverse to the longitudinal axis of the substrate 2030. The support elements 2035-1, after thermal processing, form the support structure 2040-1. In an alternative arrangement, the yarns may be weft-inserted into the substrate and have a thickness or rigidity that enables them to provide the necessary supporting function, even without thermal processing.

In another example shown in FIG. 80-3, a textile substrate 2130 having support elements 2135 may be inserted into a heated tool which has a curved surface or 3-dimensional shape. Within this tool, the textile substrate with the embedded support elements 2135 would be formed into a tubular or half-tubular shape and at the same time, the support elements 2135 of a lower melting temperature would fuse to each other, creating a level of in-built rigidity within the tubular, half-tubular or half-pipe structure in the form of support structure 2140. This structure includes concave formations 2150 and planar sections 2160. The tubular or half-tubular structure is then rolled or folded on itself and given an appropriate seam so that an air-resistant or air-tight conduit tube is formed.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A method of forming an air delivery conduit, comprising:
    applying a sealing membrane to at least first and second fabric pieces;
    thermoforming the at least first and second fabric pieces to have a curved shape; and
    welding or stitching together the at least first and second thermoformed fabric pieces to form a tubular conduit.

2. The method of forming an air delivery conduit according to claim 1, wherein the sealing membrane is one of a film laminate and a liquid silicone coating.

3. The method of forming an air delivery conduit according to claim 1, further comprising the step of enclosing a substrate in the tubular conduit to provide crush-resistance to the conduit.

4. The method of forming an air delivery conduit according to claim 3, wherein the substrate includes a base portion and upper and lower curved arms.

5. The method of forming an air delivery conduit according to claim 3, wherein the substrate includes a series of body portions connected by alternating sets of lateral links and central links.

6. The method of forming an air delivery conduit according to claim 3, wherein the substrate includes a first support member, a second support member, and at least one wave member extending between the first support member and the second support member.

7. The method of forming an air delivery conduit according to claim 6, wherein the at least one wave member includes two wave members connected to one another by at least one strut.

8. The method of forming an air delivery conduit according to claim 3, wherein the substrate includes a connector adapted for connection to a patient interface.

9. The method of forming an air delivery conduit according to claim 3, wherein the substrate is a wire coil.

10. The method of forming an air delivery conduit according to claim 9, further comprising installing a first cuff to a first end portion of the wire coil, the first cuff being adapted for connection to a patient interface and/or a manifold.

11. The method of forming an air delivery conduit according to claim 10, wherein the first cuff has a flange that abuts against the conduit and a neck portion extending from the flange that engages the end portion of the wire coil.

12. The method of forming an air delivery conduit according to claim 10, further comprising installing a second cuff to a second end portion of the wire coil, the second cuff being adapted for connection to a patient interface and/or a manifold.

13. An air delivery conduit for delivering pressurized air to a patient for treatment of sleep disordered breathing, comprising:
    at least first and second fabric pieces, each of the at least first and second fabric pieces having a sealing membrane provided thereon;
    wherein the at least first and second fabric pieces are thermoformed to have a curved shape;
    wherein the at least first and second thermoformed fabric pieces are welded or stitched to form a tubular conduit configured to convey air pressurized in the range of 2-30 cm H2O for treatment of sleep disordered breathing.

14. The air delivery conduit according to claim 13, wherein the sealing membrane is one of a film laminate and a liquid silicone coating.

15. The air delivery conduit according to claim 13, wherein a substrate is enclosed in the tubular conduit to provide crush-resistance to the conduit.

16. The air delivery conduit according to claim 15, wherein the substrate includes a base portion and upper and lower curved arms.

17. The an air delivery conduit according to claim 15, wherein the substrate includes a series of body portions connected by alternating sets of lateral links and central links.

18. The an air delivery conduit according to claim 15, wherein the substrate includes a first support member, a second support member, and at least one wave member extending between the first support member and the second support member.

19. The air delivery conduit according to claim 18, wherein the at least one wave member includes two wave members connected to one another by at least one strut.

20. The air delivery conduit according to claim 15, wherein the substrate includes a connector adapted for connection to a patient interface.

21. The air delivery conduit according to claim 15, wherein the substrate is a wire coil.

22. The air delivery conduit according to claim 21, further comprising a first cuff installed on a first end portion of the wire coil, the first cuff being adapted for connection to a patient interface and/or a manifold.

23. The air delivery conduit according to claim 22, wherein the first cuff has a flange that abuts against the conduit and a neck portion extending from the flange that engages the end portion of the wire coil.

24. The air delivery conduit according to claim 22, further comprising a second cuff installed to a second end portion of the wire coil, the second cuff being adapted for connection to a patient interface and/or a manifold.

* * * * *